(12) United States Patent
Scott

(10) Patent No.: US 8,239,028 B2
(45) Date of Patent: Aug. 7, 2012

(54) USE OF CARDIAC PARAMETERS IN METHODS AND SYSTEMS FOR TREATING A CHRONIC MEDICAL CONDITION

(75) Inventor: Timothy L. Scott, Sugarland, TX (US)

(73) Assignee: Cyberonics, Inc., Houston, TX (US)

( * ) Notice: Subject to any disclaimer, the term of this patent is extended or adjusted under 35 U.S.C. 154(b) by 379 days.

(21) Appl. No.: 12/429,998

(22) Filed: Apr. 24, 2009

(65) Prior Publication Data
US 2010/0274308 A1    Oct. 28, 2010

(51) Int. Cl.
*A61N 1/36* (2006.01)
(52) U.S. Cl. .......................................................... 607/45
(58) Field of Classification Search .................... None
See application file for complete search history.

(56) References Cited

U.S. PATENT DOCUMENTS

| | | |
|---|---|---|
| 4,172,459 A | 10/1979 | Hepp |
| 4,291,699 A | 9/1981 | Geddes et al. |
| 4,541,432 A | 9/1985 | Molina-Negro et al. |
| 4,573,481 A | 3/1986 | Bullara |
| 4,702,254 A | 10/1987 | Zabara |
| 4,867,164 A | 9/1989 | Zabara |
| 4,920,979 A | 5/1990 | Bullara |
| 4,949,721 A | 8/1990 | Toriu et al. |
| 4,979,511 A | 12/1990 | Terry, Jr. |
| 5,025,807 A | 6/1991 | Zabara |
| 5,113,869 A | 5/1992 | Nappholz et al. |
| 5,137,020 A | 8/1992 | Wayne et al. |
| 5,154,172 A | 10/1992 | Terry, Jr. et al. |
| 5,179,950 A | 1/1993 | Stanislaw |
| 5,186,170 A | 2/1993 | Varrichio et al. |
| 5,188,104 A | 2/1993 | Wernicke et al. |
| 5,203,326 A | 4/1993 | Collins |
| 5,205,285 A | 4/1993 | Baker, Jr. |
| 5,215,086 A | 6/1993 | Terry, Jr. et al. |
| 5,215,089 A | 6/1993 | Baker, Jr. |
| 5,222,494 A | 6/1993 | Baker, Jr. |
| 5,231,988 A | 8/1993 | Wernicke et al. |
| 5,235,980 A | 8/1993 | Varrichio et al. |
| 5,237,991 A | 8/1993 | Baker, Jr. et al. |

(Continued)

FOREIGN PATENT DOCUMENTS

EP    1145736    10/2001

(Continued)

OTHER PUBLICATIONS

Analysis of Heart Rate Variability in Space Medicine, R.M. Baevskii; Human Physiology, vol. 28, No. 2, 2002, pp. 202-213.*

(Continued)

*Primary Examiner* — Carl H Layno
*Assistant Examiner* — Paula J Stice
(74) *Attorney, Agent, or Firm* — Cyberonics, Inc.

(57) ABSTRACT

Disclosed herein are methods, systems, and apparatus for treating a chronic medical condition in a patient. A time of beat sequence of the patient's heart is determined. A regulatory system parameter is determined based on the time of beat sequence. The parameter is indicative of a stress level of the patient's regulatory adaptation systems. The determined regulatory system parameter is compared with a threshold regulatory system parameter value. An electrical signal is applied to a neural structure of the patient to treat the chronic medical condition if the determined regulatory system parameter exceeds the threshold regulatory system parameter value.

31 Claims, 12 Drawing Sheets

U.S. PATENT DOCUMENTS

| | | |
|---|---|---|
| 5,243,980 A | 9/1993 | Mehra |
| 5,251,634 A | 10/1993 | Weinberg |
| 5,263,480 A | 11/1993 | Wernicke et al. |
| 5,269,302 A | 12/1993 | Swartz et al. |
| 5,269,303 A | 12/1993 | Wernicke et al. |
| 5,299,569 A | 4/1994 | Wernicke et al. |
| 5,304,206 A | 4/1994 | Baker, Jr. et al. |
| 5,311,876 A | 5/1994 | Olsen et al. |
| 5,313,953 A | 5/1994 | Yomtov et al. |
| 5,330,507 A | 7/1994 | Schwartz |
| 5,330,515 A | 7/1994 | Rutecki et al. |
| 5,334,221 A | 8/1994 | Bardy |
| 5,335,657 A | 8/1994 | Terry, Jr. et al. |
| 5,404,877 A | 4/1995 | Nolan et al. |
| 5,425,373 A | 6/1995 | Causey, III |
| 5,522,862 A | 6/1996 | Testerman et al. |
| 5,540,730 A | 7/1996 | Terry, Jr. et al. |
| 5,540,734 A | 7/1996 | Zabara |
| 5,571,150 A | 11/1996 | Wernicke et al. |
| 5,611,350 A | 3/1997 | John |
| 5,645,570 A | 7/1997 | Corbucci |
| 5,651,378 A | 7/1997 | Matheny et al. |
| 5,658,318 A | 8/1997 | Stroetmann et al. |
| 5,683,422 A | 11/1997 | Rise et al. |
| 5,690,681 A | 11/1997 | Geddes et al. |
| 5,690,688 A | 11/1997 | Noren et al. |
| 5,700,282 A | 12/1997 | Zabara |
| 5,707,400 A | 1/1998 | Terry, Jr. et al. |
| 5,716,377 A | 2/1998 | Rise et al. |
| 5,720,771 A | 2/1998 | Snell |
| 5,743,860 A | 4/1998 | Hively et al. |
| 5,749,900 A * | 5/1998 | Schroeppel et al. ............ 607/4 |
| 5,792,186 A | 8/1998 | Rise |
| 5,800,474 A | 9/1998 | Benabid et al. |
| 5,833,709 A | 11/1998 | Rise et al. |
| 5,913,876 A | 6/1999 | Taylor et al. |
| 5,916,239 A | 6/1999 | Geddes et al. |
| 5,928,272 A | 7/1999 | Adkins et al. |
| 5,941,906 A | 8/1999 | Barreras, Sr. et al. |
| 5,942,979 A | 8/1999 | Luppino |
| 5,978,702 A | 11/1999 | Ward et al. |
| 5,987,352 A | 11/1999 | Klein et al. |
| 5,995,868 A | 11/1999 | Osorio et al. |
| 6,016,449 A | 1/2000 | Fischell et al. |
| 6,018,682 A | 1/2000 | Rise |
| 6,061,593 A | 5/2000 | Fischell et al. |
| 6,073,048 A | 6/2000 | Kieval et al. |
| 6,083,249 A | 7/2000 | Familoni |
| 6,091,992 A | 7/2000 | Bourgeois et al. |
| 6,104,956 A | 8/2000 | Naritoku et al. |
| 6,115,628 A | 9/2000 | Stadler et al. |
| 6,115,630 A | 9/2000 | Stadler et al. |
| 6,128,538 A | 10/2000 | Fischell et al. |
| 6,134,474 A | 10/2000 | Fischell et al. |
| 6,167,311 A | 12/2000 | Rezai |
| 6,171,239 B1 | 1/2001 | Humphrey |
| 6,175,764 B1 | 1/2001 | Loeb et al. |
| 6,205,359 B1 | 3/2001 | Boveja |
| 6,208,894 B1 | 3/2001 | Schulman et al. |
| 6,208,902 B1 | 3/2001 | Boveja |
| 6,221,908 B1 | 4/2001 | Kilgard et al. |
| 6,248,080 B1 | 6/2001 | Miesel et al. |
| 6,253,109 B1 | 6/2001 | Gielen |
| 6,269,270 B1 | 7/2001 | Boveja |
| 6,272,379 B1 | 8/2001 | Fischell et al. |
| 6,304,775 B1 | 10/2001 | Iasemidis et al. |
| 6,324,421 B1 | 11/2001 | Stadler et al. |
| 6,337,997 B1 | 1/2002 | Rise |
| 6,339,725 B1 | 1/2002 | Naritoku et al. |
| 6,341,236 B1 | 1/2002 | Osorio et al. |
| 6,356,784 B1 | 3/2002 | Lozano et al. |
| 6,356,788 B2 | 3/2002 | Boveja |
| 6,366,813 B1 | 4/2002 | DiLorenzo |
| 6,366,814 B1 | 4/2002 | Boveja |
| 6,374,140 B1 | 4/2002 | Rise |
| 6,397,100 B2 | 5/2002 | Stadler et al. |
| 6,427,086 B1 | 7/2002 | Fischell et al. |
| 6,429,217 B1 | 8/2002 | Puskas |
| 6,449,512 B1 | 9/2002 | Boveja |
| 6,459,936 B2 | 10/2002 | Fischell et al. |
| 6,463,328 B1 | 10/2002 | John |
| 6,466,822 B1 | 10/2002 | Pless |
| 6,473,639 B1 | 10/2002 | Fischell et al. |
| 6,473,644 B1 | 10/2002 | Terry, Jr. et al. |
| 6,477,418 B2 | 11/2002 | Plicchi et al. |
| 6,480,743 B1 | 11/2002 | Kirkpatrick et al. |
| 6,484,132 B1 | 11/2002 | Hively et al. |
| 6,501,983 B1 | 12/2002 | Natarajan et al. |
| 6,505,074 B2 | 1/2003 | Boveja et al. |
| 6,532,388 B1 | 3/2003 | Hill et al. |
| 6,542,774 B2 | 4/2003 | Hill et al. |
| 6,549,804 B1 | 4/2003 | Osorio et al. |
| 6,556,868 B2 | 4/2003 | Naritoku et al. |
| 6,560,486 B1 | 5/2003 | Osorio et al. |
| 6,564,102 B1 | 5/2003 | Boveja |
| 6,587,719 B1 | 7/2003 | Barrett et al. |
| 6,587,727 B2 | 7/2003 | Osorio et al. |
| 6,594,524 B2 | 7/2003 | Esteller et al. |
| 6,599,250 B2 | 7/2003 | Webb et al. |
| 6,609,025 B2 | 8/2003 | Barrett et al. |
| 6,610,713 B2 | 8/2003 | Tracey |
| 6,611,715 B1 | 8/2003 | Boveja |
| 6,615,081 B1 | 9/2003 | Boveja |
| 6,615,085 B1 | 9/2003 | Boveja |
| 6,622,038 B2 | 9/2003 | Barrett et al. |
| 6,622,041 B2 | 9/2003 | Terry, Jr. et al. |
| 6,622,047 B2 | 9/2003 | Barrett et al. |
| 6,628,985 B2 | 9/2003 | Sweeney et al. |
| 6,628,987 B1 | 9/2003 | Hill et al. |
| 6,647,296 B2 | 11/2003 | Fischell et al. |
| 6,656,125 B2 | 12/2003 | Misczynski et al. |
| 6,656,960 B2 | 12/2003 | Puskas |
| 6,668,191 B1 | 12/2003 | Boveja |
| 6,671,555 B2 | 12/2003 | Gielen et al. |
| 6,671,556 B2 | 12/2003 | Osorio et al. |
| 6,684,105 B2 | 1/2004 | Cohen et al. |
| 6,721,603 B2 | 4/2004 | Zabara et al. |
| 6,735,474 B1 | 5/2004 | Loeb et al. |
| 6,738,671 B2 | 5/2004 | Christophersom et al. |
| 6,760,626 B1 | 7/2004 | Boveja |
| 6,768,969 B1 | 7/2004 | Nikitin et al. |
| 6,788,975 B1 | 9/2004 | Whitehurst et al. |
| 6,793,670 B2 | 9/2004 | Osorio et al. |
| 6,819,953 B2 | 11/2004 | Yonce et al. |
| 6,819,956 B2 | 11/2004 | DiLorenzo |
| 6,832,114 B1 | 12/2004 | Whitehurst et al. |
| 6,836,685 B1 | 12/2004 | Fitz |
| 6,885,888 B2 | 4/2005 | Rezai |
| 6,904,390 B2 | 6/2005 | Nikitin et al. |
| 6,920,357 B2 | 7/2005 | Osorio et al. |
| 6,934,580 B1 | 8/2005 | Osorio et al. |
| 6,934,585 B1 | 8/2005 | Schloss |
| 6,944,501 B1 | 9/2005 | Pless |
| 6,957,107 B2 | 10/2005 | Rogers |
| 6,961,618 B2 | 11/2005 | Osorio et al. |
| 6,985,771 B2 | 1/2006 | Fischell et al. |
| 6,990,377 B2 | 1/2006 | Gliner et al. |
| 7,006,859 B1 | 2/2006 | Osorio et al. |
| 7,006,872 B2 | 2/2006 | Gielen et al. |
| 7,010,351 B2 | 3/2006 | Firlik et al. |
| 7,024,247 B2 | 4/2006 | Gliner et al. |
| 7,054,792 B2 | 5/2006 | Frei et al. |
| 7,058,453 B2 | 6/2006 | Nelson et al. |
| 7,076,288 B2 | 7/2006 | Skinner |
| 7,079,977 B2 | 7/2006 | Osorio et al. |
| 7,134,996 B2 | 11/2006 | Bardy |
| 7,139,677 B2 | 11/2006 | Hively et al. |
| 7,146,211 B2 | 12/2006 | Frei et al. |
| 7,146,217 B2 | 12/2006 | Firlik et al. |
| 7,146,218 B2 | 12/2006 | Esteller et al. |
| 7,149,572 B2 | 12/2006 | Frei et al. |
| 7,164,941 B2 | 1/2007 | Misczynski et al. |
| 7,167,750 B2 | 1/2007 | Knudson et al. |
| 7,174,206 B2 | 2/2007 | Frei et al. |
| 7,177,678 B1 | 2/2007 | Osorio et al. |
| 7,188,053 B2 | 3/2007 | Nikitin et al. |
| 7,204,833 B1 | 4/2007 | Osorio et al. |

| Patent/Publication | Date | Inventor(s) |
|---|---|---|
| 7,209,786 B2 | 4/2007 | Brockway |
| 7,209,787 B2 | 4/2007 | DiLorenzo |
| 7,221,981 B2 | 5/2007 | Gliner |
| 7,228,167 B2 | 6/2007 | Kara |
| 7,231,254 B2 | 6/2007 | DiLorenzo |
| 7,236,830 B2 | 6/2007 | Gliner |
| 7,236,831 B2 | 6/2007 | Firlik et al. |
| 7,242,983 B2 | 7/2007 | Frei et al. |
| 7,242,984 B2 | 7/2007 | DiLorenzo |
| 7,254,439 B2 | 8/2007 | Misczynski et al. |
| 7,263,467 B2 | 8/2007 | Sackellares et al. |
| 7,277,758 B2 | 10/2007 | DiLorenzo |
| 7,280,867 B2 | 10/2007 | Frei et al. |
| 7,282,030 B2 | 10/2007 | Frei et al. |
| 7,289,844 B2 | 10/2007 | Misczynski et al. |
| 7,292,890 B2 | 11/2007 | Whitehurst et al. |
| 7,295,881 B2 | 11/2007 | Cohen et al. |
| 7,299,096 B2 | 11/2007 | Balzer et al. |
| 7,302,298 B2 | 11/2007 | Lowry et al. |
| 7,305,268 B2 | 12/2007 | Gliner et al. |
| 7,321,837 B2 | 1/2008 | Osorio et al. |
| 7,324,850 B2 | 1/2008 | Persen et al. |
| 7,324,851 B1 | 1/2008 | DiLorenzo |
| 7,346,391 B1 | 3/2008 | Osorio et al. |
| 7,353,063 B2 | 4/2008 | Simms, Jr. |
| 7,353,064 B2 | 4/2008 | Gliner et al. |
| 7,373,199 B2 | 5/2008 | Sackellares et al. |
| 7,389,144 B1 | 6/2008 | Osorio et al. |
| 7,401,008 B2 | 7/2008 | Frei et al. |
| 7,403,820 B2 | 7/2008 | DiLorenzo |
| 7,433,732 B1 | 10/2008 | Carney et al. |
| 2002/0072782 A1 | 6/2002 | Osorio et al. |
| 2002/0099417 A1 | 7/2002 | Naritoku et al. |
| 2002/0116030 A1 | 8/2002 | Rezai |
| 2002/0128563 A1* | 9/2002 | Carlson et al. ................. 600/509 |
| 2002/0151939 A1 | 10/2002 | Rezai |
| 2002/0188214 A1 | 12/2002 | Misczynski et al. |
| 2003/0074032 A1 | 4/2003 | Gliner |
| 2003/0083716 A1 | 5/2003 | Nicolelis et al. |
| 2003/0083726 A1 | 5/2003 | Zeijlemaker et al. |
| 2003/0125786 A1 | 7/2003 | Gliner et al. |
| 2003/0130706 A1 | 7/2003 | Sheffield et al. |
| 2003/0144829 A1 | 7/2003 | Geatz et al. |
| 2003/0181954 A1 | 9/2003 | Rezai |
| 2003/0181958 A1 | 9/2003 | Dobak |
| 2003/0208212 A1 | 11/2003 | Cigaina |
| 2003/0210147 A1 | 11/2003 | Humbard |
| 2003/0212440 A1 | 11/2003 | Boveja |
| 2003/0236558 A1 | 12/2003 | Whitehurst et al. |
| 2004/0006278 A1 | 1/2004 | Webb et al. |
| 2004/0088024 A1 | 5/2004 | Firlik et al. |
| 2004/0122484 A1 | 6/2004 | Hatlestad et al. |
| 2004/0122485 A1 | 6/2004 | Stahmann et al. |
| 2004/0133119 A1 | 7/2004 | Osorio et al. |
| 2004/0138516 A1 | 7/2004 | Osorio et al. |
| 2004/0138517 A1 | 7/2004 | Osorio et al. |
| 2004/0138647 A1 | 7/2004 | Osorio et al. |
| 2004/0138711 A1 | 7/2004 | Osorio et al. |
| 2004/0153129 A1 | 8/2004 | Pless et al. |
| 2004/0158119 A1 | 8/2004 | Osorio et al. |
| 2004/0158165 A1 | 8/2004 | Yonce et al. |
| 2004/0172085 A1 | 9/2004 | Knudson et al. |
| 2004/0172091 A1 | 9/2004 | Rezai |
| 2004/0172094 A1 | 9/2004 | Cohen et al. |
| 2004/0176812 A1 | 9/2004 | Knudson et al. |
| 2004/0176831 A1 | 9/2004 | Gliner et al. |
| 2004/0199212 A1 | 10/2004 | Fischell et al. |
| 2004/0249302 A1 | 12/2004 | Donoghue et al. |
| 2004/0249416 A1 | 12/2004 | Yun et al. |
| 2005/0004621 A1 | 1/2005 | Boveja et al. |
| 2005/0020887 A1 | 1/2005 | Goldberg |
| 2005/0021092 A1 | 1/2005 | Yun et al. |
| 2005/0021103 A1 | 1/2005 | DiLorenzo |
| 2005/0021104 A1 | 1/2005 | DiLorenzo |
| 2005/0021105 A1 | 1/2005 | Firlik et al. |
| 2005/0021106 A1 | 1/2005 | Firlik et al. |
| 2005/0021107 A1 | 1/2005 | Firlik et al. |
| 2005/0021118 A1 | 1/2005 | Genau et al. |
| 2005/0027284 A1 | 2/2005 | Lozano et al. |
| 2005/0033378 A1 | 2/2005 | Sheffield et al. |
| 2005/0033379 A1 | 2/2005 | Lozano et al. |
| 2005/0038484 A1 | 2/2005 | Knudson et al. |
| 2005/0049515 A1 | 3/2005 | Misczynski et al. |
| 2005/0049655 A1 | 3/2005 | Boveja et al. |
| 2005/0065562 A1 | 3/2005 | Rezai |
| 2005/0065573 A1 | 3/2005 | Rezai |
| 2005/0065574 A1 | 3/2005 | Rezai |
| 2005/0065575 A1 | 3/2005 | Dobak |
| 2005/0070971 A1 | 3/2005 | Fowler et al. |
| 2005/0075701 A1 | 4/2005 | Shafer |
| 2005/0075702 A1 | 4/2005 | Shafer |
| 2005/0101873 A1 | 5/2005 | Misczynski et al. |
| 2005/0119703 A1 | 6/2005 | DiLorenzo |
| 2005/0124901 A1 | 6/2005 | Misczynski et al. |
| 2005/0131467 A1 | 6/2005 | Boveja et al. |
| 2005/0131485 A1 | 6/2005 | Knudson et al. |
| 2005/0131486 A1 | 6/2005 | Boveja et al. |
| 2005/0131493 A1 | 6/2005 | Boveja et al. |
| 2005/0143786 A1 | 6/2005 | Boveja et al. |
| 2005/0148893 A1 | 7/2005 | Misczynski et al. |
| 2005/0148894 A1 | 7/2005 | Misczynski et al. |
| 2005/0148895 A1 | 7/2005 | Misczynski et al. |
| 2005/0153885 A1 | 7/2005 | Yun et al. |
| 2005/0154425 A1 | 7/2005 | Boveja et al. |
| 2005/0154426 A1 | 7/2005 | Boveja et al. |
| 2005/0165458 A1 | 7/2005 | Boveja et al. |
| 2005/0187590 A1 | 8/2005 | Boveja et al. |
| 2005/0192644 A1 | 9/2005 | Boveja et al. |
| 2005/0197590 A1 | 9/2005 | Osorio et al. |
| 2005/0245971 A1 | 11/2005 | Brockway et al. |
| 2005/0261542 A1 | 11/2005 | Riehl |
| 2005/0277998 A1 | 12/2005 | Tracey et al. |
| 2005/0283200 A1 | 12/2005 | Rezai et al. |
| 2005/0283201 A1 | 12/2005 | Machado et al. |
| 2005/0288600 A1 | 12/2005 | Zhang et al. |
| 2005/0288760 A1 | 12/2005 | Machado et al. |
| 2006/0009815 A1 | 1/2006 | Boveja |
| 2006/0074450 A1 | 4/2006 | Boveja |
| 2006/0079936 A1 | 4/2006 | Boveja |
| 2006/0094971 A1 | 5/2006 | Drew |
| 2006/0095081 A1 | 5/2006 | Zhou et al. |
| 2006/0106430 A1 | 5/2006 | Fowler et al. |
| 2006/0135877 A1 | 6/2006 | Giftakis et al. |
| 2006/0135881 A1 | 6/2006 | Giftakis et al. |
| 2006/0155495 A1 | 7/2006 | Osorio et al. |
| 2006/0167497 A1 | 7/2006 | Armstrong et al. |
| 2006/0173493 A1 | 8/2006 | Armstrong et al. |
| 2006/0173522 A1 | 8/2006 | Osorio |
| 2006/0190056 A1 | 8/2006 | Fowler et al. |
| 2006/0195163 A1 | 8/2006 | KenKnight et al. |
| 2006/0200206 A1 | 9/2006 | Firlik et al. |
| 2006/0212091 A1 | 9/2006 | Lozano et al. |
| 2006/0224067 A1 | 10/2006 | Giftakis et al. |
| 2006/0224191 A1 | 10/2006 | DiLorenzo |
| 2006/0241697 A1 | 10/2006 | Libbus et al. |
| 2006/0241725 A1 | 10/2006 | Libbus et al. |
| 2006/0293720 A1 | 12/2006 | DiLorenzo |
| 2007/0027486 A1 | 2/2007 | Armstrong et al. |
| 2007/0027497 A1 | 2/2007 | Parnis et al. |
| 2007/0027498 A1 | 2/2007 | Maschino et al. |
| 2007/0027500 A1 | 2/2007 | Maschino et al. |
| 2007/0032834 A1 | 2/2007 | Gliner et al. |
| 2007/0043392 A1 | 2/2007 | Gliner et al. |
| 2007/0055320 A1 | 3/2007 | Weinand et al. |
| 2007/0073150 A1 | 3/2007 | Gopalsami et al. |
| 2007/0073355 A1 | 3/2007 | DiLorenzo |
| 2007/0088403 A1 | 4/2007 | Wyler et al. |
| 2007/0100278 A1 | 5/2007 | Frei et al. |
| 2007/0100392 A1 | 5/2007 | Maschino et al. |
| 2007/0142862 A1 | 6/2007 | DiLorenzo |
| 2007/0142873 A1 | 6/2007 | Esteller et al. |
| 2007/0150024 A1 | 6/2007 | Leyde et al. |
| 2007/0150025 A1 | 6/2007 | DiLorenzo et al. |
| 2007/0161919 A1 | 7/2007 | DiLorenzo |
| 2007/0162086 A1 | 7/2007 | DiLorenzo |
| 2007/0167991 A1 | 7/2007 | DiLorenzo |
| 2007/0173901 A1* | 7/2007 | Reeve ............................. 607/45 |
| 2007/0173902 A1 | 7/2007 | Maschino et al. |

| | | | |
|---|---|---|---|
| 2007/0179534 | A1 | 8/2007 | Firlik et al. |
| 2007/0179557 | A1 | 8/2007 | Maschino et al. |
| 2007/0179558 | A1 | 8/2007 | Gliner et al. |
| 2007/0208212 | A1 | 9/2007 | DiLorenzo |
| 2007/0213785 | A1 | 9/2007 | Osorio et al. |
| 2007/0233192 | A1 | 10/2007 | Craig |
| 2007/0239210 | A1 | 10/2007 | Libbus et al. |
| 2007/0244407 | A1 | 10/2007 | Osorio |
| 2007/0249953 | A1 | 10/2007 | Osorio et al. |
| 2007/0249954 | A1 | 10/2007 | Virag et al. |
| 2007/0255147 | A1 | 11/2007 | Drew et al. |
| 2007/0255155 | A1 | 11/2007 | Drew et al. |
| 2007/0260147 | A1 | 11/2007 | Giftakis et al. |
| 2007/0260289 | A1 | 11/2007 | Giftakis et al. |
| 2007/0265536 | A1 | 11/2007 | Giftakis et al. |
| 2007/0272260 | A1 | 11/2007 | Nikitin et al. |
| 2007/0282177 | A1 | 12/2007 | Pilz |
| 2008/0033503 | A1 | 2/2008 | Fowler et al. |
| 2008/0033508 | A1 | 2/2008 | Frei et al. |
| 2008/0046055 | A1 | 2/2008 | Fowler et al. |
| 2008/0064934 | A1 | 3/2008 | Frei et al. |
| 2008/0071323 | A1 | 3/2008 | Lowry et al. |
| 2008/0077028 | A1 | 3/2008 | Schaldach et al. |
| 2008/0103548 | A1 | 5/2008 | Fowler et al. |
| 2008/0114417 | A1 | 5/2008 | Leyde |
| 2008/0119900 | A1 | 5/2008 | DiLorenzo |
| 2008/0125820 | A1 | 5/2008 | Stahmann et al. |
| 2008/0139870 | A1 | 6/2008 | Gliner et al. |
| 2008/0146959 | A1 | 6/2008 | Sheffield et al. |
| 2008/0161712 | A1 | 7/2008 | Leyde |
| 2008/0161713 | A1 | 7/2008 | Leyde et al. |
| 2008/0161879 | A1 | 7/2008 | Firlik et al. |
| 2008/0161880 | A1 | 7/2008 | Firlik et al. |
| 2008/0161881 | A1 | 7/2008 | Firlik et al. |
| 2008/0161882 | A1 | 7/2008 | Firlik et al. |
| 2008/0183096 | A1 | 7/2008 | Snyder et al. |
| 2008/0183097 | A1 | 7/2008 | Leyde et al. |

FOREIGN PATENT DOCUMENTS

| | | |
|---|---|---|
| EP | 1486232 | 12/2004 |
| GB | 2026870 | 2/1980 |
| GB | 2079610 | 1/1982 |
| WO | 00/64336 | 11/2000 |
| WO | 2004/036377 | 4/2004 |
| WO | 2005/007120 | 1/2005 |
| WO | 2005/053788 | 6/2005 |
| WO | 2005/067599 | 7/2005 |
| WO | 2006/050144 | 5/2006 |
| WO | 2006/122148 | 11/2006 |
| WO | 2007/066343 | 6/2007 |
| WO | 2007/072425 | 6/2007 |
| WO | 2007/124126 | 11/2007 |
| WO | 2007/124190 | 11/2007 |
| WO | 2007/124192 | 11/2007 |
| WO | 2007/142523 | 12/2007 |
| WO | 2008/045597 | 4/2008 |

OTHER PUBLICATIONS

Regulation of Autonomic Nervous System in Space an Magnetic Storms; Adv. Space Res, vol. 22, No. 2 pp. 227-234; 1998.*

Method of Evaluation of the Functional State Requlatory Body of Biological Object; Russian Patent Application No. RU 2103911, published Nov. 8, 1993 to Baevsky et. al.*

Method of Evaluation of the Functional State Requlatory Body of Biological Object; Russian Patent Application No. RU 2103911, published Nov. 8, 1993 to Baevsky et. al. machine translation.*

Bachman, D.,S. et al.; "*Effects of Vagal Volleys and Serotonin on Units of Cingulate Cortex in Monkeys;*" Brain Research , vol. 130 (1977). pp. 253-269.

Baevskii, R.M. "*Analysis of Heart Rate Variability in Space Medicine;*" Human Physiology, vol. 28, No. 2, (2002); pp. 202-213.

Baevsky, R.M., et al.; "*Autonomic Cardiovascular and Respiratory Control During Prolonged Spaceflights Aboard the International Space Station;*"J. Applied Physiological, vol. 103, (2007) pp. 156-161.

Boon, P., et al.; "*Vagus Nerve Stimulation for Epilepsy, Clinical Efficacy of Programmed and Magnet Stimulation;*" (2001); pp. 93-98.

Boon, Paul, et al.; "*Programmed and Magnet-Induced Vagus Nerve Stimulation for Refractory Epilepsy;*"Journal of Clinical Neurophysiology vol. 18 No. 5; (2001); pp. 402-407.

Borovikova, L.V., et al.; "*Vagus Nerve Stimulation Attenuates the Systemic Inflammatory Response to Endotoxin;*" Letters to Nature; vol. 405; (May 2000); pp. 458-462.

Chakravarthy, N., et al.; "*Controlling Synchronization in a Neuron-Level Population Model;*" International Journal of Neural Systems, vol. 17, No. 2 (2007) pp. 123-138.

Clark, K.B., et al.; "*Posttraining Electrical Stimulation of Vagal Afferents with Concomitant Vagal Efferent Inactivation Enhances Memory Storage Processes in the Rat;*" Neurobiology of Learning and Memory, vol. 70, 364-373 (1998) Art. No. NL983863.

Elmpt, W.J.C., et al.; "*A Model of Heart Rate Changes to Detect Seizures in Severe Epilepsy*" Seizure vol. 15, (2006) pp. 366-375.

Frei, M.G., et al.; "*Left Vagus Nerve Stimulation with the Neurocybernetic Prosthesis Has Complex Effects on Heart Rate and on Its Variability in Humans:*" Epilepsia, vol. 42, No. 8 (2001); pp. 1007-1016.

George, M.S., et al.; "*Vagus Nerve Stimulation: A New Tool for Brain Research and Therapy;*"Society of Biological Psychiatry vol. 47 (2000) pp. 287-295.

Henry, Thomas R.; "*Therapeutic Mechanisms of Vague Name Stimulation;*". Neurology, vol. 59 (Supp 4) (Sep. 2002), pp. S3-S14.

Hallowitz et al., "*Effects of Vagal Volleys on Units of Intralaminar and Juxtalaminar Thalamic Nuclei in Monkeys;*"Brain Research, vol. 130 (1977), pp. 271-286.

Iasemidis; L.D., et al.; "*Dynamical Resetting of the Human Brain at Epilepctic Seizures: Application of Nonlinear Dynamics and Global Optimization Techniques;*" IEEE Transactions on Biomedical Engineering, vol. 51, No. 3 (Mar. 2004); pp. 493-506.

Iasemidis; L.D., et al.; "*Spatiotemporal Transition to Epileptic Seizures: A Nonlinear Dynamical Analysis of Scalp and Intracranial EEG Recordings;*"Spatiotemporal Models in Biological and Artificial Systems; F.L. Silva et al. (Eds.) IOS Press, 1997; pp. 81-88.

Iasemidis, L.D.; "Epileptic *Seizure Prediction and Control*" IEEE Transactions on Biomedical Engineering, vol. 50, No. 5 (May 2003); pp. 549-558.

Kautzner, J., et al.; "*Utility of Short-Term Heart Rate Variability for Prediction of Sudden Cardiac Death After Acute Myocardial Infarction*"Acta Univ. Palacki. Olomuc., Fac. Med., vol. 141 (1998) pp. 69-73.

Koenig, S.A., et al.; "*Vagus Nerve Stimulation Improves Severely Impaired Heart Rate Variability in a Patient with Lennox-Gastaut-Syndrome*" Seizure (2007) Article in Press—YSEIZ-1305; pp. 1-4.

Koo, B., "*EEG Changes With Vagus Nerve Stimulation*" Journal of Clinical Neurophysiology, vol. 18 No. 5 (Sep. 2001); pp. 434-441.

Krittayaphong, M.D., et al.; "*Heart Rate Variability in Patients with Coronary Artery Disease: Differences in Patients with Higher and Lower Depression Scores*" Psychosomatic Medicine vol. 59 (1997) pp. 231-235.

Leutmezer, F., et al.; "*Electrocardiographic Changes at the Onset of Epileptic Seizures;*" Epilepsia, vol. 44, No. 3; (2003); pp. 348-354.

Lewis, M.E., et al.; "*Vagus Nerve Stimulation Decreases Left Ventricular Contractility in Vivo in the Human and Pig Heart*" The Journal of Physiology vol. 534, No. 2, (2001) pp. 547-552.

Li, M., et al.; "*Vagal Nerve Stimulation Markedly Improves Long-Term Survival After Chronic Heart Failure in Rats:*" Circulation (Jan. 2004) pp. 120-124.

Licht, C.M.M.; *Association Between Major Depressive Disorder and Heart Rate Variability in the Netherlands Study of Depression and Anxiety (NESDA)*; Arch. Gen Psychiatry, vol. 65, No. 12 (Dec. 2008); pp. 1358-1367.

Lockard et al., "*Feasibility and Safety of Vagal Stimulation in Monkey Model;*" Epilepsia, vol. 31 (Supp. 2) (1990), pp. S20-S26.

McClintock, P., "*Can Noise Actually Boost Brain Power*" Physics World Jul. 2002; pp. 20-21.

Mori, T., et al.; "*Noise-Induced Entrainment and Stochastic Resonance in Human Brain Waves*" Physical Review Letters vol. 88, No. 21 (2002); pp. 218101-1-218101-4.

Mormann, F., "Seizure prediction: the long and winding road," Brain 130 (2007), 314-333.

Nouri, M.D.; "Epilepsy and the Autonomic Nervous System" emedicine (updated May 5, 2006); pp. 1-14; http://www.emedicine.com/neuro/topic658.htm.

O'Regan, M.E., et al.; "Abnormalities in Cardiac and Respiratory Function Observed During Seizures in Childhood" Developmental Medicine & Child Neurlogy, vol. 47 (2005) pp. 4-9.

Pathwardhan, R.V., et al., Control of Refractory status epilepticus precipitated by anticonvulasnt withdrawal using left vagal nerve stimulation: a case report, Surgical Neurology 64 (2005) 170-73.

Poddubnaya, E.P., "Complex Estimation of Adaptation Abilities of the Organism in Children Using the Indices of Responsiveness of the Cardiovascular System and Characteristics of EEG" Neurophysiology vol. 38, No. 1 (2006); pp. 63-74.

Rugg-Gunn, F.J., et al.; "Cardiac Arrhythmias in Focal Epilepsy: a Prospective Long-Term Study" www.thelancet.com vol. 364 (2004) pp. 2212-2219.

Sajadieh, A., et al.; "Increased Heart Rate and Reduced Heart-Rte Variability are Associated with Subclinical Inflammation in Middle-Aged and Elderly Subjects with No Apparent Heart Disease" European Heart Journal vol. 25, (2004); pp. 363-370.

Schernthaner, C., et al.; "Autonomic Epilepsy—The Influence of Epileptic Discharges on Heart Rate and Rhythm"The Middle European Joural of Medicine vol. 111, No. 10 (1999) pp. 392-401.

Terry et al.; "The Implantable Neurocybernetic Prosthesis System", Pacing and Clinical Electrophysiology, vol. 14, No. 1 (Jan. 1991), pp. 86-93.

Tubbs, R.S., et al.; "Left-Sided Vagus Nerve Stimulation Decreases Intracranial Pressure Without Resultant Bradycardia in the Pig: A Potential Therapeutic Modality for Humans" Child's Nervous System Original Paper; Springer-Verlag 2004.

Umetani, M.D., et al.; "Twenty-Four Hour Time Domain Heart Rate Variability and Heart Rate: Relations to Age and Gender Over Nince Decades"JACC vol. 31, No. 3; (Mar. 1998); pp. 593-601.

Vonck, K., et al. "The Mechanism of Action of Vagus Nerve Stimulation for Refractory Epilepsy—The Current Status", Journal of Neurophysiology, vol. 18 No. 5 (2001), pp. 394-401.

Woodbury, et al., "Vagal Stimulation Reduces the Severity of Maximal Electroshock Seizures in Intact Rats. Use of a Cuff Electrode for Stimulating and Recording"; Pacing and Clinical Electrophysiology, vol. 14 (Jan. 1991), pp. 94-107.

Zabara, J.; "Neuroinhibition of Xylaine Induced Emesis" Pharmacology & Toxicology, vol. 63 (1988) pp. 70-74.

Zabara, J. "Inhibition of Experimental Seizures in Canines by Repetivie Vagal Stimulation" Epilepsia vol. 33, No. 6 (1992); pp. 1005-1012.

Zabara, J., et al.; "Neural Control of Circulation I"The Physiologist, vol. 28 No. 4 (1985); 1 page.

Zabara, J., et al.; "Neuroinhibition in the Regulation of Emesis" Space Life Sciences, vol. 3 (1972) pp. 282-292.

Osorio, Ivan et al., "An Introduction to Contingent (Closed-Loop) Brain Electrical Stimulation for Seizure Blockage, to Ultra-Short-Term Clinical Trials, and to Multidimensional Statistical Analysis of Therapeutic Efficacy," Journal of Clinical Neurophysiology, vol. 18, No. 6, pp. 533-544, 2001.

Osorio, Ivan et al., "Automated Seizure Abaatement in Humans Using Electrical Stimulation," Annals of Neurology, vol. 57, No. 2, pp. 258-268, 2005.

Sunderam, Sridhar et al., "Vagal and Sciatic Nerve Stimulation Have Complex, Time-Dependent Effects on Chemically-Induced Seizures: A Controlled Study," Brain Research, vol. 918, pp. 60-66, 2001.

Weil, Sabine et al, "Heart Rate Increase in Otherwise Sublinical Seizures is Different in Temporal Versus Extratemporal Seizure Onset: Support for Temporal Lobe Automatic Influence," Epileptic Disord., vol. 7, No. 3, Sep. 2005, pp. 199-204.

Digenarro, Giancarlo et al., "Ictal Heart Rate Increase Precedes EEG Discharge in Drug-Resistant Mesial Temporal Lobe Seizures," Clinical Neurophysiology, No. 115, 2004, pp. 1169-1177.

Zijlmans, Maeike et al., "Heart Rate Changes and ECG Abnormalities During Epileptic Seizures: Prevalence and Definition of an Objective Clinical Sign," Epilepsia, vol. 43, No. 8, 2002, pp. 847-854.

O'Donovan, Cormac A. et al., "Computerized Seizure Detection Based on Heart Rate Changes," abstract of AES Proceedings, Epilepsia, vol. 36, Suppl. 4, 1995, p. 7.

Robinson, Stephen E et al., "Heart Rate Variability Changes as Predictor of Response to Vagal Nerve Stimulation Therapy for Epilepsy," abstract of AES Proceedings,Epilepsia, vol. 40, Suppl. 7, 1999, p. 147.

Long, Teresa J. et al., "Effectiveness of Heart Rate Seizure Detection Compared to EEG in an Epilepsy MoitoringUnit (EMU)," abstract of AES Proceedings, Epilepsia, vol. 40, Suppl. 7, 1999, p. 174.

* cited by examiner

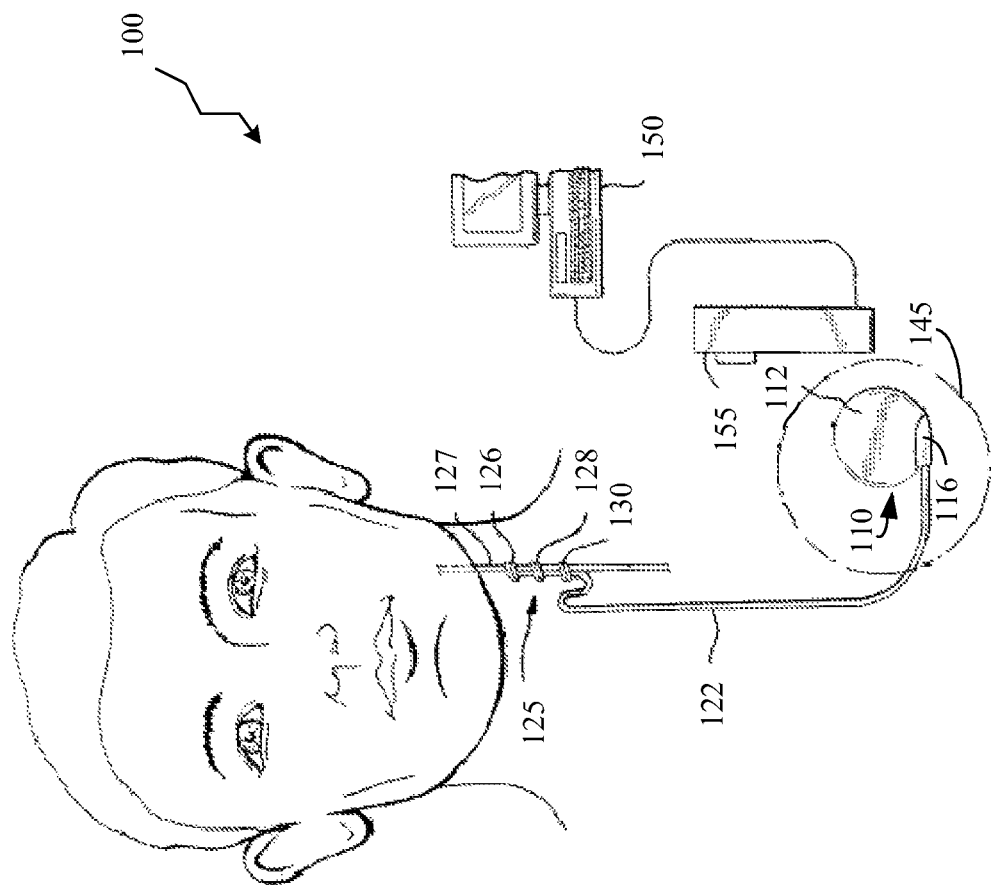

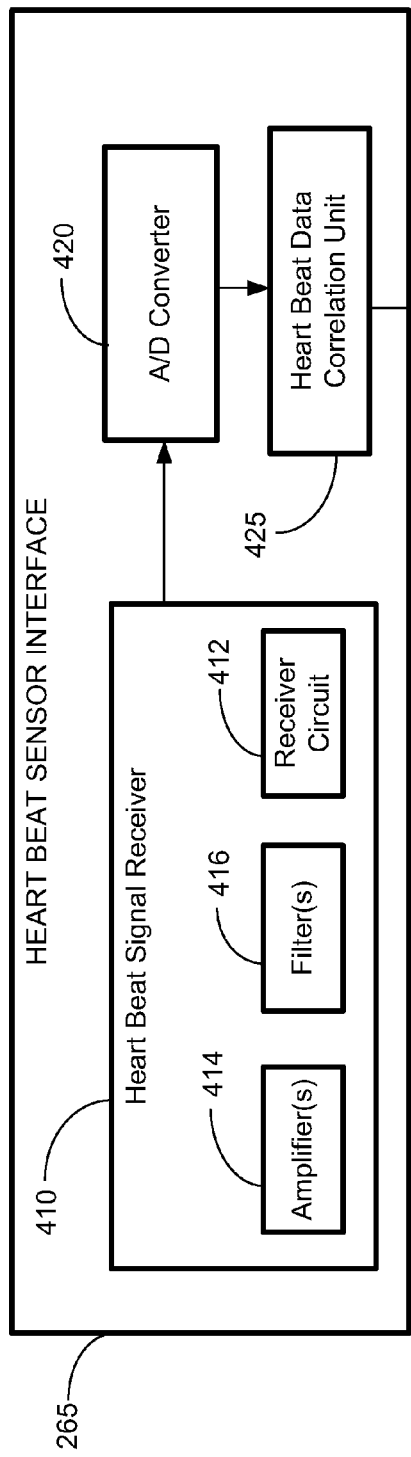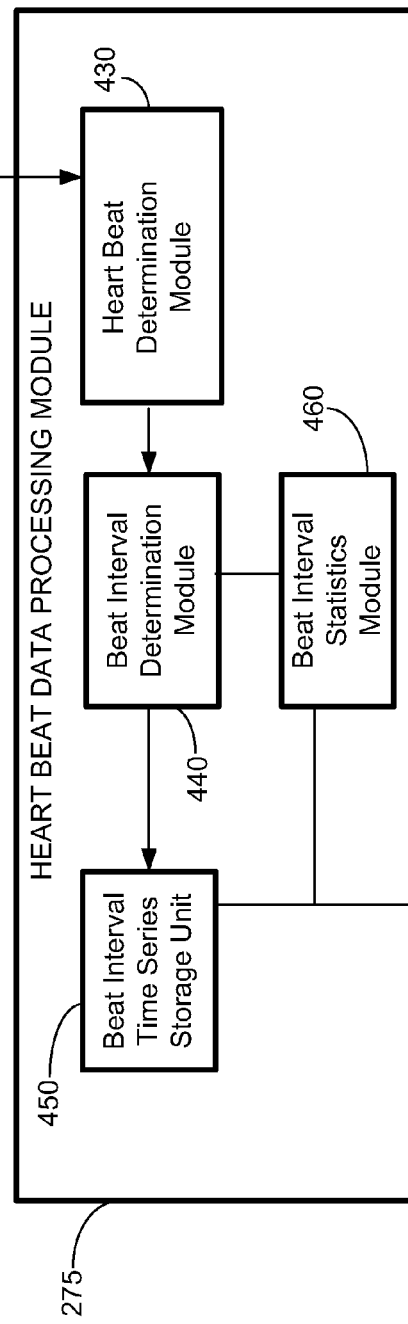
FIGURE 4A
FIGURE 4B

USE OF CARDIAC PARAMETERS IN METHODS AND SYSTEMS FOR TREATING A CHRONIC MEDICAL CONDITION

FIELD OF THE INVENTION

This invention relates generally to medical device systems and, more particularly, to medical device systems capable of determining and/or treating a chronic medical condition.

DESCRIPTION OF THE RELATED ART

Many advancements have been made in treating diseases such as depression and epilepsy. Therapies using electrical signals for treating these diseases have been found to be effective. Implantable medical devices have been effectively used to deliver therapeutic stimulation to various portions of the human body (e.g., the vagus nerve) for treating these diseases. As used herein, "stimulation," "neurostimulation," "stimulation signal," or "neurostimulation signal" refers to the application of an electrical, mechanical, magnetic, electromagnetic, photonic, audio, and/or chemical signal to a neural structure in the patient's body. The signal is an exogenous signal that is distinct from the endogenous electrical, mechanical, and chemical activity (e.g., afferent and/or efferent electrical action potentials) generated by the patient's body and environment. In other words, the stimulation signal (whether electrical, mechanical, magnetic, electromagnetic, photonic, audio or chemical in nature) applied to the nerve in the present invention is a signal applied from an artificial source, e.g., a neurostimulator.

A "therapeutic signal" refers to a stimulation signal delivered to a patient's body with the intent of treating a medical condition by providing a modulating effect to neural tissue. The effect of a stimulation signal on neuronal activity is termed "modulation"; however, for simplicity, the terms "stimulating" and "modulating", and variants thereof, are sometimes used interchangeably herein. In general, however, the delivery of an exogenous signal itself refers to "stimulation" of the neural structure, while the effects of that signal, if any, on the electrical activity of the neural structure are properly referred to as "modulation." The modulating effect of the stimulation signal upon the neural tissue may be excitatory or inhibitory, and may potentiate acute and/or long-term changes in neuronal activity. For example, the "modulating" effect of the stimulation signal to the neural tissue may comprise one more of the following effects: (a) initiation of an action potential (afferent and/or efferent action potentials); (b) inhibition or blocking of the conduction of action potentials, whether endogenous or exogenously induced, including hyperpolarizing and/or collision blocking, (c) affecting changes in neurotransmitter/neuromodulator release or uptake, and (d) changes in neuro-plasticity or neurogenesis of brain tissue.

In some embodiments, electrical neurostimulation may be provided by implanting an electrical device, i.e., an implantable medical device (IMD), underneath the skin of a patient and delivering an electrical signal to a nerve such as a cranial nerve. Generally, electrical neurostimulation signals that perform neuromodulation are delivered by the IMD via one or more leads, although leadless neurostimulators have also been developed. The leads generally terminate at their distal ends in one or more electrodes, and the electrodes, in turn, are electrically coupled to tissue in the patient's body. For example, a number of electrodes may be attached to various points of a nerve or other tissue inside a human body for delivery of a neurostimulation signal.

While feedback stimulation (i.e., an electrical signal applied in response to a sensed body parameter such as heart rate) schemes have been proposed, conventional vagus nerve stimulation (VNS) usually involves non-feedback stimulation characterized by a number of parameters. Specifically, conventional vagus nerve stimulation usually involves a series of grouped electrical pulses defined by an "on-time" and an "off-time." Each sequence of pulses during an on-time may be referred to as a "pulse burst." The burst is followed by the off-time period in which no signals are applied to the nerve. During the on-time, electrical pulses of a defined electrical current (e.g., 0.5-2.0 milliamps) and pulse width (e.g., 0.25-1.0 milliseconds) are delivered at a defined frequency (e.g., 20-30 Hz) for the on-time duration, usually a specific number of seconds, e.g., 10-60 seconds. The pulse bursts are separated from one another by the off-time, (e.g., 30 seconds-5 minutes) in which no electrical signal is applied to the nerve. The on-time and off-time parameters together define a duty cycle, which is the ratio of the on-time to the combination of the on-time and off-time, and which describes the percentage of time that the electrical signal is applied to the nerve.

In conventional VNS, the on-time and off-time may be programmed to define an intermittent pattern in which a repeating series of electrical pulse bursts are generated and applied to a cranial nerve such as the vagus nerve. The off-time is provided to allow the nerve to recover from the stimulation of the pulse burst, and to conserve power. If the off-time is set at zero, the electrical signal in conventional VNS may provide continuous stimulation to the vagus nerve. Alternatively, the off time may be as long as one day or more, in which case the pulse bursts are provided only once per day or at even longer intervals. Typically, however, the ratio of "off-time" to "on-time" may range from about 0.5 to about 10.

In addition to the on-time and off-time, the other parameters defining the electrical signal in conventional VNS may be programmed over a range of values. The pulse width for the pulses in a pulse burst of conventional VNS may be set to a value not greater than about 1 msec, such as about 250-500 μsec, and the number of pulses in a pulse burst is typically set by programming a frequency in a range of about 20-150 Hz (i.e., 20 pulses per second to 150 pulses per second). A non-uniform frequency may also be used. Frequency may be altered during a pulse burst by either a frequency sweep from a low frequency to a high frequency, or vice versa. Alternatively, the timing between adjacent individual signals within a burst may be randomly changed such that two adjacent signals may be generated at any frequency within a range of frequencies.

Although neurostimulation has proven effective in the treatment of a number of medical conditions, it would be desirable to further enhance and optimize neurostimulation for this purpose. For example, it may be desirable to further enhance treatment of chronic medical conditions. Generally, the state of the art implantable medical devices lack efficient treatment based on certain feedback from the patient's body for treating chronic conditions. This may be due to either a belief that no reliable body parameter is a reliable indicator or predictor of the disease state of the chronic medical condition; the difficulty of isolating a particular indicator from many factors that contribute to the disease state; a belief that feedback systems will provide no benefit over non-feedback treatment for chronic medical conditions; or to combinations of the foregoing. In sharp contrast to this general neglect of feedback-based treatments for chronic illnesses, designers have proposed numerous systems to provide treatment of certain episodic or acute medical conditions based upon feedback of certain body parameters. For example, many different feedback schemes for detection and treatment of epileptic seizures have been proposed, including feedback based upon EEG signals, heart rate, and sensing of neural activity. Further, the relative shortage of reliable treatments for many chronic medical conditions may also contribute to the absence of feedback-based treatment options for chronic medical conditions. This lack of sufficient knowledge as to the treatment of chronic or non-episodic type ailments presents difficult challenges in analyzing body parameters to provide feedback-based treatment for such conditions. There is a need for improved treatment options, including feedback-based treatment options, for many chronic medical conditions.

SUMMARY OF THE INVENTION

In one aspect of the present invention, a method for treating a chronic medical condition in a patient is provided. A time of beat sequence of the patient's heart is determined. A regulatory system parameter is determined based on the time of beat sequence. The parameter is indicative of a stress level of the patient's regulatory adaptation systems. The determined regulatory system parameter is compared with a threshold regulatory system parameter value. An electrical signal is applied to a neural structure of the patient to treat the chronic medical condition if the determined regulatory system parameter exceeds the threshold regulatory system parameter value.

In another aspect of the present invention, another method for treating a chronic medical condition in a patient is provided. A time of beat sequence of the patient's heart is determined. A heart rate variability (HRV) parameter is determined based on the time of beat sequence. The HRV parameter is associated with a parasympathetic function of the patient. The determined HRV parameter is compared with a threshold HRV parameter value. An electrical signal is applied to a neural structure to treat the chronic medical condition if the determined HRV parameter exceeds the threshold HRV value.

In another aspect of the present invention, an implantable medical device (IMD) for treating a chronic medical condition in a patient is provided. The IMD comprises a sensing module for sensing data relating to a time of beat sequence of the patient's heart and a heart beat data processing module to process the data relating to the time of beat sequence. The IMD also includes a heart parameter module adapted to determine at least one heart parameter selected from a heart rate variability (HRV) parameter associated with a parasympathetic function of the patient and a regulatory system parameter indicative of a stress level of the patient's regulatory adaptation systems. The heart parameter module is also adapted to determine the at least one heart parameter based upon the processed data relating to the time of beat sequence of the patient's heart. The IMD also includes a comparator adapted to compare the heart parameter determined by the heart parameter module with a threshold heart parameter value. The IMD also includes an electrical signal module adapted to generate and apply an electrical signal to a neural structure to treat the chronic medical condition in the patient based upon the comparison of the determined heart parameter value and the threshold heart parameter value.

In yet another aspect of the present invention, a computer readable program storage device is provided that is encoded with instructions that, when executed by a computer, perform a method for treating a chronic medical condition in a patient is provided. The method includes determining a time of beat sequence of the patient's heart and determining a first index of regulatory activity systems (IARS) value associated with the patient based upon the time of beat sequence. The method also includes comparing the first IARS value to a first threshold IARS value and providing a therapy to the patient in response to a determination that the first IARS value exceeds the first threshold IARS value.

In yet another aspect of the present invention, a computer readable program storage device is provided that is encoded with instructions that, when executed by a computer, perform a method for treating a chronic medical condition in a patient is provided. The method includes determining a time of beat sequence of the patient's heart and determining an HRV parameter indicative of parasympathetic activity from the time of beat sequence. The method also includes comparing the determined HRV value to a threshold HRV value; and providing a therapy to the patient in response to a determination that the HRV value is below the threshold HRV value.

In yet another aspect of the present invention, an implantable medical device system is provided for providing an indication of a level of stress upon a regulatory system of a patient having a chronic medical condition. The system includes an implantable medical device (IMD) that comprises a sensing module for sensing data relating to a time of beat sequence of the patient's heart and a heart beat data processing module adapted to process the data relating to the time of beat sequence. The IMD also includes a regulatory activity module adapted to determine an index of regulatory activity systems (IARS) value associated with the patient based upon the data relating to the time of beat sequence of the patient's heart. The IARS value is indicative of level of stress upon the regulatory system of the patient. The IMD also includes a communication module adapted to provide the IARS value to at least one of a patient or a healthcare provider. The medical device is adapted to provide a treatment to the patient in response to a determination that the IRS value indicates a chronic condition in the patient.

BRIEF DESCRIPTION OF THE DRAWINGS

The invention may be understood by reference to the following description taken in conjunction with the accompanying drawings, in which like reference numerals identify like elements, and in which:

FIG. 1A provides a stylized diagram of an implantable medical device implanted into a patient's body for providing a therapeutic electrical signal to a neural structure of the patient's body, in accordance with one illustrative embodiment of the present invention;

FIG. 4A illustrates a stylized block diagram of a heart beat sensor interface of a medical device, in accordance with one illustrative embodiment of the present invention;

FIG. 4B illustrates a stylized block diagram of a heart beat data processing module of a medical device, in accordance with one illustrative embodiment of the present invention;

Figure 1B:
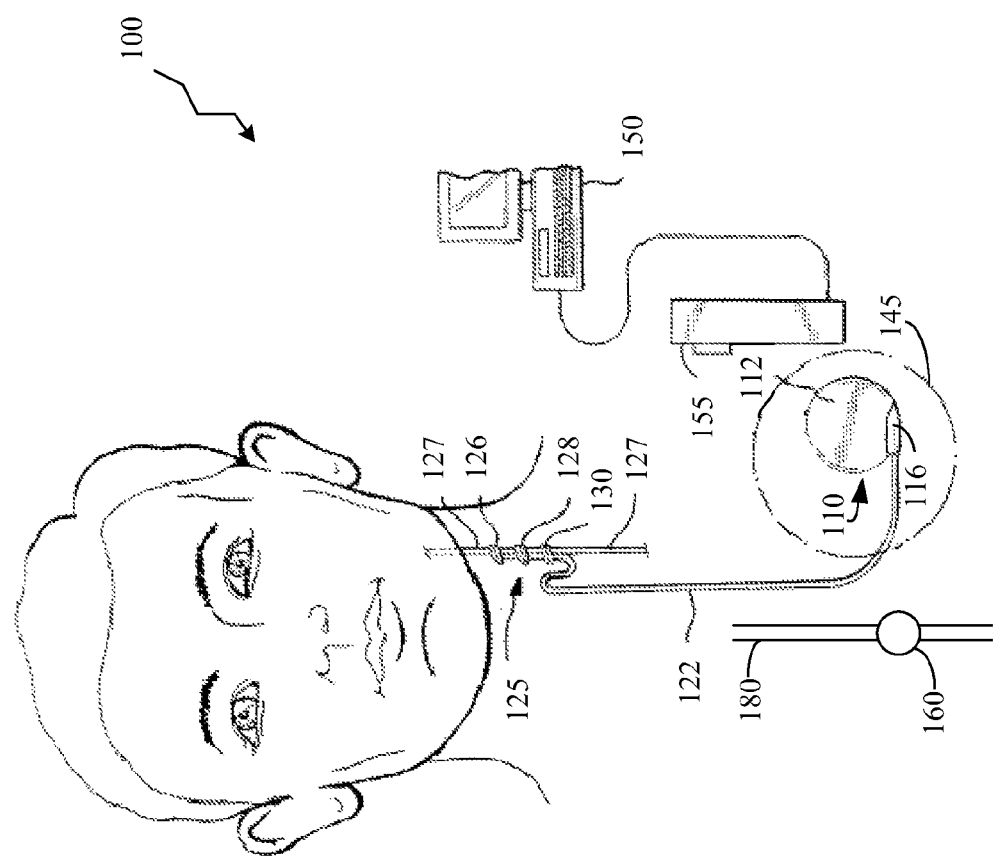
FIG. 1B provides a stylized diagram of an implantable medical device implanted into a patient's body for providing a therapeutic electrical signal to a neural structure of the patient's body, in accordance with another illustrative embodiment of the present invention.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF SPECIFIC EMBODIMENTS

Illustrative embodiments of the invention are described herein. In the interest of clarity, not all features of an actual implementation are described in this specification. In the development of any such actual embodiment, numerous implementation-specific decisions must be made to achieve the design-specific goals, which will vary from one implementation to another. It will be appreciated that such a development effort, while possibly complex and time-consuming, would nevertheless be a routine undertaking for persons of ordinary skill in the art having the benefit of this disclosure.

This document does not intend to distinguish between components that differ in name but not function. In the following discussion and in the claims, the terms "including" and "includes" are used in an open-ended fashion, and thus should be interpreted to mean "including, but not limited to." Also, the term "couple" or "couples" is intended to mean either a direct or an indirect electrical connection. "Direct contact," "direct attachment," or providing a "direct coupling" indicates that a surface of a first element contacts the surface of a second element with no substantial attenuating medium there between. The presence of small quantities of substances, such as bodily fluids, that do not substantially attenuate electrical connections does not vitiate direct contact. The word "or" is used in the inclusive sense (i.e., "and/or") unless a specific use to the contrary is explicitly stated.

The term "electrode" or "electrodes" described herein may refer to one or more stimulation electrodes (i.e., electrodes for delivering an electrical signal generated by an IMD to a tissue), sensing electrodes (i.e., electrodes for sensing a physiological indication of a patient's body), and/or electrodes that are capable of delivering a stimulation signal, as well as performing a sensing function.

Cranial nerve stimulation has been proposed to treat a number of medical conditions pertaining to or mediated by one or more structures of the nervous system of the body, including epilepsy and other movement disorders, depression, anxiety disorders and other neuropsychiatric disorders, dementia, traumatic brain injury, coma, migraine headache, obesity, eating disorders, sleep disorders, cardiac disorders (such as congestive heart failure and atrial fibrillation), hypertension, endocrine disorders (such as diabetes and hypoglycemia), and pain (including neuropathic pain and fibromyalgia), among others. See, e.g., U.S. Pat. Nos. 4,867,164; 5,299,569; 5,269,303; 5,571,150; 5,215,086; 5,188,104; 5,263,480; 6,587,719; 6,609,025; 5,335,657; 6,622,041; 5,916,239; 5,707,400; 5,231,988; and 5,330,515. Despite the numerous disorders for which cranial nerve stimulation has been proposed or suggested as a treatment option, the fact that detailed neural pathways for many (if not all) cranial nerves remain relatively unknown, makes predictions of efficacy for any given disorder difficult or impossible. Moreover, even if such pathways were known, the precise stimulation parameters that would modulate particular pathways relevant to a particular disorder generally cannot be predicted.

In some embodiments, electrical neurostimulation may be provided by implanting an electrical device underneath the skin of a patient and delivering an electrical signal to a nerve such as a cranial nerve. In another alternative embodiment, the signal may be generated by an external pulse generator outside the patient's body, coupled by an RF or wireless link to an implanted electrode.

Embodiments of the present invention provide for treating a chronic or a non-episodic condition using heart beat signals. In one embodiment, heart beat signals indicative of heart rate variability (HRV) ("HRV signals") are used to treat chronic or non-episodic medical condition(s). In one embodiment, HRV signals may be used to treat chronic or non-episodic conditions that adversely affect the parasympathetic system of a patient's body.

HRV may be related to the degree of tension of the regulatory systems (or regulatory adaptation system) affected by the activation of the pituitary-adrenal system. This activation may occur in response to a stress and/or in reaction to a response of the sympathoadrenal system. Under stress, a person having a sufficient functional reserve would respond with a normal working tension or stress of the regulatory system. For this person, in rest, the tension or stress of the regulatory system would be relatively low. However, a person with a medical condition, and particularly a chronic medical condition, may display a relatively high tension of the regulatory system, even under situations that, absent the patient's medical condition, would be non-stressful, e.g., rest or mild activity. HRV may also refer to a functional system (described in further detail below) that relates to numerous regulatory mechanisms affecting the circulatory system (e.g., regulation of blood circulation). One HRV variable or regulatory system parameter useful in embodiments of the present invention is the index of activity of regulatory system (IARS), which relates to values reflecting different degrees of tension of the regulatory system and the adaptation ability of a patient's body.

As an illustrative example of an embodiment of the present invention, HRV signals may be analyzed using various methods to decipher a state of the regulatory system of a patient's body. The "state" may refer to the stability or instability of a patient's regulatory system, which may relate to the stress upon the regulatory system. Based upon the state of the regulatory system of a patient's body, a determination may be made that a particular treatment may be provided to treat a chronic condition. Chronic conditions that are treatable by embodiments of the present invention include, but are not limited to, congestive heart failure, traumatic brain injury (TBI), depression, stroke, fibromyalgia, obesity, etc. These diseases, although they occasionally may manifest certain episodic instances, are generally chronic diseases that are related to the regulatory system. Particularly, these diseases may be associated with compromised functioning of at least a portion of the parasympathetic nervous system of a patient.

The HRV signals can be gathered by any of a number of techniques. For example, data relating to a beat sequence (or HRV signals) may be gathered by an electrocardiogram (ECG) device. In one embodiment, the data relating to the beat sequence (or HRV signals) may be related to the R-waves of the beat sequence, such as a time series of R-waves or a series of R-R intervals. Those skilled in the art having the benefit of the present disclosure would appreciate that other time series of waves may be used and still remain within the spirit and scope of the present invention.

Data relating to R-waves may be gathered by an ECG device or, in one embodiment, by a vagus nerve stimulator, such as described in U.S. patent application Ser. No. 12/258,019, filed Oct. 24, 2008, which is hereby incorporated by reference herein.

The R-R interval variations of a patient's heart beat are influenced by vagal activity. Moreover, the vagal activity may prompt inhibitions of sympathetic nervous system activity. In other words, utilizing information present in HRV data, influences upon the sympathetic and the parasympathetic activity of the human body may be determined. In treatment of chronic conditions, such as diabetes, a reduction in value of the time domain parameters of the HRV may carry a negative prognostic value. Thus, the value of the time domain parameters of the HRV, as well as other HRV parameters described herein, may be used as indicator(s) to characterize various chronic conditions, such as diabetes. Further, variance in the absolute power of the low frequency (LF) and the high frequency (HF) values in diabetic patients may also exist, and the LF:HF ratio may be indicative of a negative prognostic value.

Further, value of parameter resulting from statistical analysis of HRV data may also be indicative of one or more chronic conditions. Using a series of instantaneous heart rates or intervals of heart beat cycle, statistical measures relating to HRV may be determined. For example, statistical time domain HRV parameters may be calculated using direct measurements of normal-to-normal (NN) intervals or from the differences between NN intervals. One example of a statistical time domain parameter is the standard deviation of the NN intervals, i.e., the square root of the variance between NN intervals. These types of HRV parameters are described in further details below.

Moreover, geometric methods of analyzing HRV data may also be performed to determine if the HRV data indicates a chronic condition. For example, NN intervals may be converted into a geometric pattern. These patterns may include sample density of distribution of NN intervals durations, sample density distributions of differences between adjacent NN intervals, Lorenz plot of NN or RR intervals, etc. Geometric analysis of HRV data may include converting a measurement of the geometric pattern (e.g., width of the distribution histogram) into an HRV parameter, interpolating a geometric pattern using mathematic shape defining techniques (e.g., approximation of the distribution histogram using a triangle method or an exponential curve) to define an HRV parameter, and/or classifying the geometric shape into pattern based categories (e.g., elliptic, linear, triangular shapes of Lorentz plots) that represent different types of heart rate variations. The results from applying geometric methods for analyzing HRV data may provide indications of one or more chronic conditions in a patient.

Spectral components of the HRV may also be relatively low for cardiac patients and, therefore, spectral analysis of the HRV resulting in low volumes of parameters may be indicative of heart conditions. In other words, a reduced HRV parameter value may be indicative of compromised cardiac functioning, or of a rising level of stress upon the cardiac regulatory systems. The LF component in the spectral analysis, for example, may be relatively low in cardiac patients. Oscillations in the spectral LF components of the HRV may be indicative of chronic cervical spinal cord disorders, e.g., lesions. These are examples of variations in the HRV components that may be detected, and this information may be used to treat various chronic conditions, such as depression, anxiety disorders and other neuropsychiatric disorders, dementia, traumatic brain injury, coma, obesity, chronic cardiac disorders (such as congestive heart failure), hypertension, chronic endocrine disorders (such as diabetes), and chronic pain (including neuropathic pain and fibromyalgia), among others. Utilizing embodiments of the present invention, treatment of chronic conditions, particularly chronic conditions that adversely affect the parasympathetic system of the patient, may be performed. Influences upon the regulatory system of the patient may be detected based upon HRV data, and appropriate therapy may be applied to reduce and treat one or more chronic conditions.

Receiving the data relating to the beat sequence of the patient's heart (or "HRV signals" per previous discussion) may comprise sensing a time of beat sequence of a patient's heart and generating a time series data stream from said time of beat sequence. In a further embodiment, receiving the data relating to the beat sequence of the patient's heart may comprise receiving a series of R-R intervals, and generating the time series data stream may comprise sensing a plurality of R peaks from the R-R intervals and using the R peaks for providing time stamps to generate the time series data stream based upon the time stamps.

From the R-R interval data, various classes of HRV parameters may be determined. Known classes include time domain HRV parameters, which may include statistical parameters (e.g., PNN50, SDNN, SDANN, RMSSD and logarithmic index), geometric HRV parameters (such as those derived from Lorenz plots); frequency domain HRV parameters, which primarily involve spectral parameters derived from power spectral density analysis (such as the high frequency (HF), low frequency (LF, very low frequency (VLF), and ultra low frequency (ULF) components, and various ratios of the foregoing); rhythm pattern HRV parameters, such is the interval spectrum and spectrum of counts; and nonlinear HRV parameters, which include parameters derived from Fourier spectra analysis, H scaling exponents, Coarse Graining Spectral Analysis, Poincare sections, low-dimension attractor plots, singular value decomposition, attractor trajectories, D2 correlation dimension, Lyapunov exponents, and Kolmogorov entropy. Summaries of different HRV parameters are widely available in the cardiology literature. See, e.g., the 1996 publication by the Task Force of the European Society of Cardiology and the North American Society of Pacing Electrophysiology entitled "Heart Rate Variability, Standards of Measurement, Physiological Interpretation and Clinical Use."

Without being bound by theory, it is believed that vagal activity influences a variety of aspects of chronic medical conditions through a variety of mechanisms, such as modulation of neurotransmitter production and effects upon inflammatory cytokine production. In the present invention, HRV parameters conveying information about vagal activity and function, including its relative activity as compared to sympathetic neural function, are those primarily intended for incorporation into embodiments of the present invention. Many other HRV parameters from the foregoing broad classes of HRV parameters are indicative of one or more aspects of sympathetic and/or parasympathetic functioning, and it should be appreciated that those specifically listed here are non-limiting examples.

One useful sub-class of time domain HRV parameters includes statistical parameters, which may be calculated easily from heart beat data and which provide many parameters useful in embodiments of the present invention. Based upon the heartbeat data, the QRS complex may be evaluated and normal-to-normal (NN) intervals may be determined. Normal-to-normal intervals may refer to intervals between adjacent corresponding QRS complexes (respectively). Using the NN intervals, a statistical measure that results in a percentage parameter relating to an NN 50 count divided by the total number of all NN intervals, may be determined, i.e., PNN50. In an alternative embodiment, PNN50 may refer to the number of NN interval pairs with a difference exceeding 50 ms, divided by the total number of NN intervals. The PNN50 value may be indicative of the degree of the predominance of the parasympathetic (i.e., vagal) portion of the patient's autonomic regulation over the sympathetic portion of the autonomic regulation.

Further, using the NN intervals, another statistical measure that results in a time parameter (ms) using a standard deviation of all NN intervals, may be determined, i.e., SDNN. The SDNN value may relate to the total effect of the autonomic regulation of blood circulation of the patient's body.

Moreover, the square root of the sum of differences of a sequential series of the NN intervals may also be calculated to provide RMSSD. The RMSSD may relate to the activity of the parasympathetic portion of the autonomic regulation of a patient's body.

Spectral HRV parameters comprise another class of HRV parameters yielding useful information for embodiments of the present invention. One example of the spectral parameter may include a low frequency (LF) power variability component. This component may be expressed as percentage of the low-frequency power variability in relation to the total power fluctuations. Another example of the spectral parameter may include a high frequency (HF) power variability component. The HF power component is generally regarded as an indication of vagal activity. This component may be expressed as percentage of the high-frequency power variability in relation to the total power fluctuations. Further a frequency ratio may be determined by calculating a ratio of the low frequency and high frequency power components with the magnification of a central frequency of each component.

Nonlinear HRV parameters may also provide information useful in embodiments of the present invention. In addition to the parameters described above, other non-linear parameters exist and may be strongly correlated, either positively or negatively, with one or more of the above-referenced time domain and/or spectral domain HRV parameters. However, it must be borne in mind that many of the other parameters that exist have relatively weak or essentially no correlation with any of the above parameters. In general, HRV parameters, regardless of which class or sub-class they are part, are useful in the present invention when they possess a relatively high correlation with other parameters known to be indicative of one or more aspects of parasympathetic function or its relationship to sympathetic function. It should be noted that whether any two HRV parameters have a strong correlation, a weak correlation, or essentially no correlation cannot be determined a priori for any particular medical condition, and instead must be derived from empirical observation and application of concepts provided by embodiments of the present invention. It must further be borne in mind that variability in the value of a parameter over a period of time has no a priori correlation with the patient's heart beat over the same period of time.

In order to treat a chronic or non-episodic condition, an index of activity of regulatory systems (IARS) value for a particular patient may be determined. IARS is a parameter that was developed in the context of space medicine to study the effects of space on the human body. More particularly, there was a desire to study the stress on a person's regulatory system due to travel in space. The prior analysis of IARS was directed to the study of stress of regulatory system in relation to pre-nosologic states. That is, prior application and studies of IARS was directed to non-disease contexts to analyze the effects of space travel on the human body. Utilizing embodiments of the present invention, IARS values may be used to provide feedback and/or treatment of chronic or non-episodic conditions. Specific IARS value(s) of a patient may be determined to determine the presence and/or severity of a chronic or non-episodic condition of a patient. Further, a predetermined threshold IARS value for that patient may be determined. In other embodiments, the threshold IARS value may be a dynamic value that may be changed over time. The threshold IARS can be established by a physician based on one or more of the particular parameter(s) under consideration, the patient's age, the patient's sex, the condition of the patient's heart, the severity of the patient's medical disorder, a blood parameter, health status of the patient, IARS history of the patient, and/or other parameters.

Based on a comparison of the determined IARS valued to a predetermined threshold value, a treatment action for the chronic medial condition may be performed. Embodiments of the present invention provide for one or more types of treatment therapies that may be provided to treat the chronic condition. These treatments may include applying an electrical signal to at least a brain structure, a cranial nerve, a spinal cord of a patient, a sympathetic nerve, and/or a peripheral nerve of a patient. The application of the treatment may also include an analysis wherein an HRV parameter (e.g., PNN50) is below a predetermined threshold. The processing of the HRV signal includes analysis of the IARS or the value relating to the HRV signal. These analyses provide for an indication that treatment of a chronic condition may be desirable. Based upon this indication, various treatment regimens may be implemented by the IMD to treat the chronic or the non-episodic condition.

Treatment for a chronic condition may include one of a plurality of types of electrical signal, wherein various characteristics of the electrical signal (e.g., frequency, pulse-width, on-time, off-time, amplitude, etc.) may be controlled based upon the type and severity of the chronic condition. Further, other types of treatment, e.g., drugs and/or cooling of a neural structure of the patient, may be implemented in addition or alternative to the electrical signal therapy described herein. The particular type of delivery of drug treatments, the type of drugs and/or cooling of a neural structure may be provided by those skilled in the art having benefit of the present disclosure.

Although not so limited, a system capable of implementing embodiments of the present invention is described below. FIG. 1A depicts a stylized implantable medical system (IMD) 100 for implementing one or more embodiments of the present invention. An electrical signal generator 110 is provided, having a main body 112 comprising a case or shell with a header 116 for connecting to an insulated, electrically conductive lead assembly 122. The generator 110 is implanted in the patient's chest in a pocket or cavity formed by the implanting surgeon just below the skin (indicated by a dotted line 145), similar to the implantation procedure for a pacemaker pulse generator.

A nerve electrode assembly 125, preferably comprising a plurality of electrodes having at least an electrode pair, is conductively connected to the distal end of the lead assembly 122, which preferably comprises a plurality of lead wires (one wire for each electrode). Each electrode in the electrode assembly 125 may operate independently or alternatively, may operate in conjunction with the other electrodes. In one embodiment, the electrode assembly 125 comprises at least a cathode and an anode. In another embodiment, the electrode assembly comprises one or more unipolar electrodes.

Lead assembly 122 is attached at its proximal end to connectors on the header 116 of generator 110. The electrode assembly 125 may be surgically coupled to the vagus nerve 127 in the patient's neck or at another location, e.g., near the patient's diaphragm or at the esophagus/stomach junction. Other (or additional) cranial nerves such as the trigeminal and/or glossopharyngeal nerves may also be used to deliver the electrical signal in particular alternative embodiments. In one embodiment, the electrode assembly 125 comprises a bipolar stimulating electrode pair 126, 128 (i.e., a cathode and an anode). Suitable electrode assemblies are available from Cyberonics, Inc., Houston, Tex., USA as the Model 302 electrode assembly. However, persons of skill in the art will appreciate that many electrode designs could be used in the present invention. In one embodiment, the two electrodes are wrapped about the vagus nerve, and the electrode assembly 125 may be secured to the vagus nerve 127 by a spiral anchoring tether 130 such as that disclosed in U.S. Pat. No. 4,979,511 issued Dec. 25, 1990 to Reese S. Terry, Jr. and assigned to the same assignee as the instant application. Lead assembly 122 may be secured, while retaining the ability to flex with movement of the chest and neck, by a suture connection to nearby tissue (not shown).

In some embodiments, the electrode assembly 125 may comprise temperature sensing elements and/or heart beat sensor elements. Other sensors for other body parameters may also be employed. Both passive and active stimulation may be combined or delivered by a single IMD according to the present invention. Either or both modes may be appropriate to treat a specific patient under observation.

Figure 3:
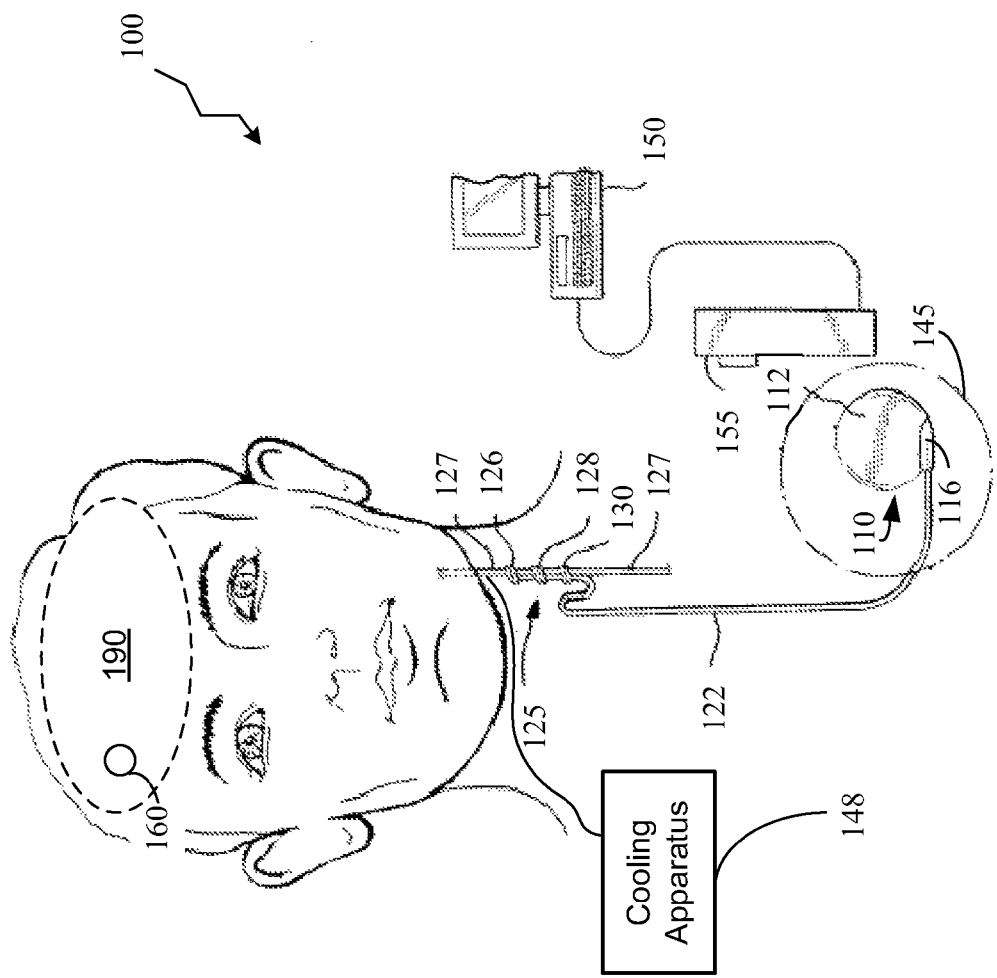
FIG. 3 provides a stylized diagram of an implantable medical device implanted into a patient's body for providing a therapeutic electrical signal to a neural structure of the patient's body, in accordance with yet another illustrative embodiment of the present invention.

In alternative embodiments, the implantable medical device system further comprises an electrical stimulator comprising an electrode 160 (not to scale) adapted to be coupled to the spinal cord 180 (FIG. 1B) or to a region of the brain 190 (FIG. 3). The physician can select precise locations for coupling to the spinal cord 180 or brain 190 based on his or her observations of the patient's medical condition, among other values. In various embodiments, the implantable medical device system may comprise one, two, or three of the IMD 100, the spinal cord stimulator, and the brain stimulator. The system 100 may also comprise a cooling apparatus 148 (FIG. 3) that is capable of cooling a neural structure of the patient.

The electrical pulse generator 110 may be programmed with an external device (ED) such as computer 150 using programming software known in the art. A programming wand 155 may be coupled to the computer 150 as part of the ED to facilitate wireless radio frequency (RF) communication between the computer 150 and the implanted pulse generator 110. The programming wand 155 and computer 150 permit non-invasive communication with the generator 110 after the latter is implanted. In systems where the computer 150 uses one or more channels in the Medical Implant Communications Service (MICS) bandwidths, the programming wand 155 may be omitted to permit more convenient communication directly between the computer 150 and the pulse generator 110.

Figure 2:
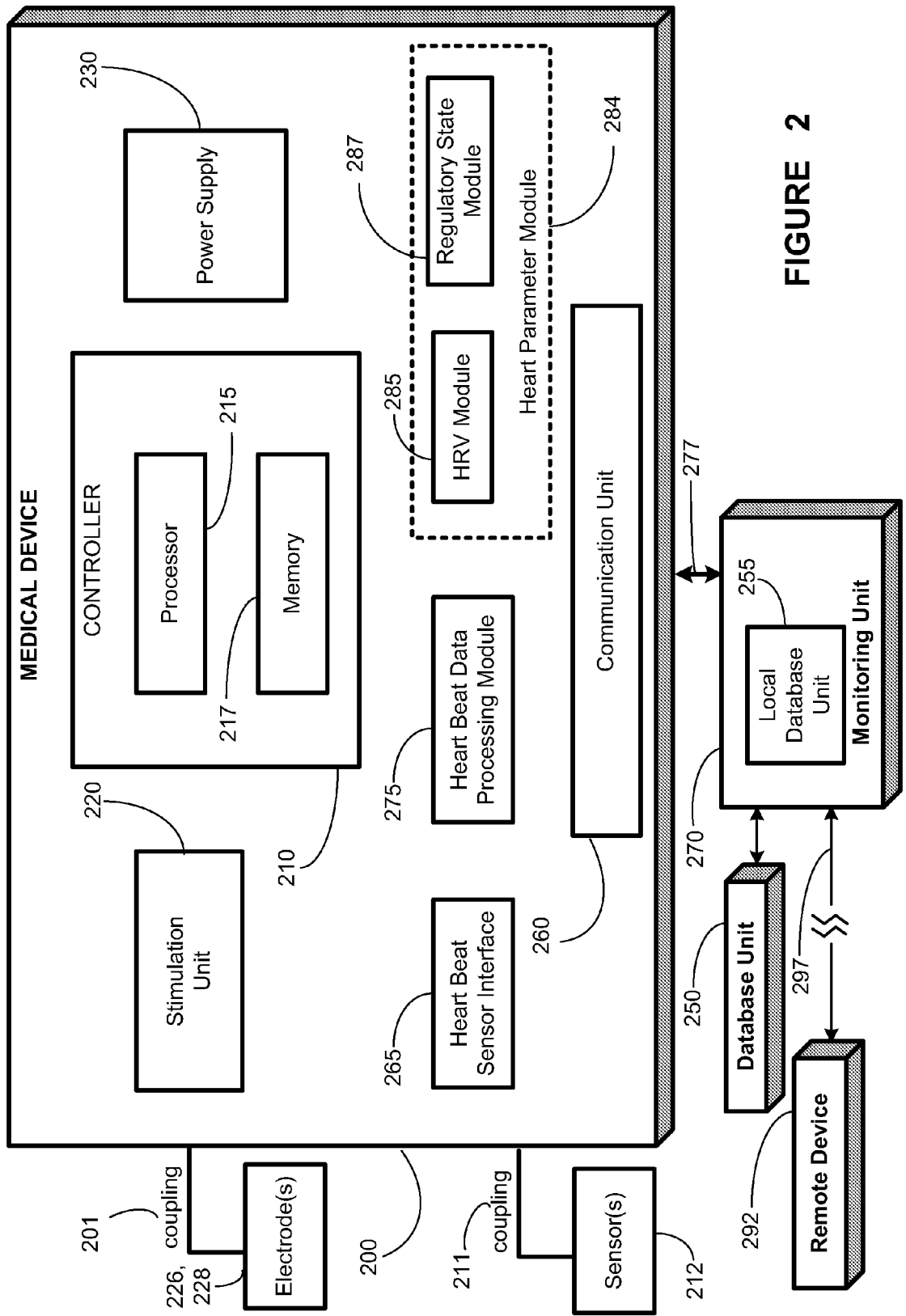
FIG. 2 is a block diagram of a medical device system that includes a medical device and a monitoring device, in accordance with one illustrative embodiment of the present invention.

Turning now to FIG. 2, a block diagram depiction of the medical device (MD) 200 is provided, in accordance with one illustrative embodiment of the present invention. The MD 200 (such as implantable generator 110 from FIG. 1) may comprise a controller 210 capable of controlling various aspects of the operation of the MD 200. The controller 210 is capable of receiving data and causing a stimulation unit 220 to generate and deliver an electrical signal to target tissues of the patient's body for treating a medical condition. For example, the controller 210 may receive instructions from another device such as Monitoring Unit 270, or may cause the electrical signal to be generated and delivered based on calculations and programming internal to MD 200. The controller 210 is capable of affecting substantially all functions of the MD 200. The MD 200 may be an external device, or in an alternative embodiment, an implantable medical device.

The controller 210 may comprise various components, such as a processor 215, a memory 217, etc. The processor 215 may comprise one or more microcontrollers, microprocessors, etc., capable of performing various executions of software components. The memory 217 may comprise various memory portions where a number of types of data (e.g., internal data, external data instructions, software codes, status data, diagnostic data, etc.) may be stored. The memory 217 may comprise one or more of random access memory (RAM), dynamic random access memory (DRAM), electrically erasable programmable read-only memory (EEPROM), flash memory, etc.

The MD 200 may also comprise a stimulation unit 220 capable of generating and delivering electrical signals to one or more electrodes 126, 128 via a coupling 201. In one embodiment, MD 200 may be an implantable medical device, and coupling 201 may comprise a lead assembly such as lead assembly 122 (FIG. 1). In another embodiment, MD 200 may be external to the patient's body, and may be coupled to an implanted lead via an inductive coupling such as an RF inductive coupling. Whether MD 200 is an implantable or external unit, a therapeutic electrical signal may be delivered to the electrodes 226, 228 by the stimulation unit 220 based upon instructions from the controller 210. The stimulation unit 220 may comprise various circuitry, such as electrical signal generators, impedance control circuitry to control the impedance "seen" by the leads, and other circuitry that receives instructions relating to the delivery of the electrical signal to tissue.

In other embodiments, coupling 201 is operatively coupled to an electrode, wherein the electrode is adapted to couple to at least one of a portion of a brain structure of the patient, a cranial nerve of a patient, a spinal cord of a patient, a sympathetic nerve structure of the patient, or a peripheral nerve of the patient.

The MD 200 may also comprise a power supply 230. The power supply 230 may comprise a battery, voltage regulators, capacitors, etc., to provide power for the operation of the MD 200, including delivering the therapeutic electrical signal. The power supply 230 comprises a power source that in some embodiments may be rechargeable. In other embodiments, a non-rechargeable power source may be used. The power supply 230 provides power for the operation of the MD 200, including electronic operations and the electrical signal generation and delivery functions. The power supply 230 may comprise a lithium/thionyl chloride cell or a lithium/carbon monofluoride (LiCFx) cell for implantable embodiments, and more common watch batteries or 9 volt batteries for non-implantable embodiments. Other battery types known in the art of implantable medical devices may also be used.

The MD 200 may also comprise a communication unit 260 capable of facilitating communications between the MD 200 and various devices. In particular, the communication unit 260 is capable of providing transmission and reception of electronic signals to and from a monitoring unit 270, such as computer 150 and a wand 155 that can communicate with the MD 200 remotely (FIG. 1). The communication unit 260 may include hardware, software, firmware, or any combination thereof.

The MD 200 may also comprise one or more sensor(s) 212 coupled via sensor coupling 211 (which may comprise a lead or an inductive coupling) to the MD 200. The sensor(s) 212 are capable of receiving signals related to a physiological parameter, such as the patient's heart beat, and delivering the signals to the MD 200. In one embodiment, the sensor(s) 212 may be the same as electrode(s) 226, 228. In other embodiments, the sensor(s) 212 are separate structures that may be placed in, on, or near the patient's heart, or outside the patient's skin, such as over the patient's heart or elsewhere on the patient's torso.

In one embodiment, the MD 200 may comprise a heart beat sensor interface 265 that is capable of receiving signals related to the patient's heart beat from the sensor(s) 212. The heart beat sensor interface 265 may be capable of performing any necessary or suitable amplifying, filtering, and performing analog-to-digital (A/D) conversions to prepare the signals for downstream processing. The heart beat sensor interface, in one embodiment, may comprise software module(s) that are capable of performing various interface functions, filtering functions, etc., to process heart beat signals. In another embodiment the heart beat sensor interface 265 may comprise hardware circuitry that is capable of performing these functions. In yet another embodiment, the heart beat sensor interface 265 may comprise hardware, firmware, software and/or any combination thereof. A more detailed illustration of the heart beat sensor interface 265 is provided in FIG. 4 and accompanying description below.

The heartbeat sensor interface 265 is capable of receiving heartbeat signals and providing the signal to a heart beat data processing module 275 that the MD 200 may comprise. Based upon the signals processed by the heart beat sensor interface 265, a heart beat data processing module 275 may determine various properties of the patient's heart beat time series and store such properties or forward them on for further processing/analysis. In one embodiment, the heart beat data processing module 275 is capable of processing the heart beat into various components such as those necessary to determine HRV parameters and/or parameters indicative of stress upon a regulatory system. For example, the heart beat data processing module 275 is capable of processing the heart beat signals such that IARS values and or HRV parameters may be determined. For example, parameters such as PNN50, SDNN, SDANN, RMSSD, HF spectral power, interval spectrum, and Lyapunov exponents that may be indicative of a chronic or non-episodic physiological event involving vagal function may be determined by the heart beat data processing module 275.

Moreover, the MD 200 may also comprise a heart parameter module 284. Two submodules, HRV module 285 and regulatory state module 287, may be provided as part of heart parameter module 284. It may be appreciated that heart parameter module 284 may also comprise other modules for determination of heart parameters in addition to those determined by HRV module 285 and regulatory state module 287. The HRV module 285 is capable of determining one or more HRV parameters from the data derived from the heart beat signal. Further description of the HRV module 285 is provided in FIG. 5A and accompanying description below.

The MD 200 also comprises a regulatory state module 287. The regulatory state module 287 is capable of using the data processed by the heart beat data processing module 275 to determine whether the patient's regulatory adaptation system is under stress or has become unstable. This determination may be made using a variety of algorithms. The regulatory state module 287 may perform a comparison of a calculated regulatory parameter value such an IARS value to a predetermined or adaptive threshold regulatory parameter value.

The regulatory state module 287 may perform an adaptive adjustment of the threshold regulatory parameter value based upon various factors, such as various physiological data relating to the patient and environmental data such as time of day and time of year. The physiological data may include the age of the patient, the height, weight, blood pressure, normal heart rate, general health, stress levels, etc. In this manner, a dynamic threshold may be adapted in order to determine whether the regulatory state of the patient is under stress based upon the threshold value. When the regulatory state module 287 determines that the patient's regulatory system is under excessive stress or has become unstable, the MD 200 may provide a predetermined therapeutic electrical signal to stimulate at least a portion of the patient's vagus nerve. The electrical signal may be adjusted in such a manner to affect the parasympathetic system of the patient to provide a reduction in the stress level of the regulatory system of the patient, or to reduce the instability of the patient's regulatory system.

In various embodiments, one or more of the units or modules described above may be located in an monitoring unit 270 or a remote device 292, with communications between that unit or module and communication unit 260 in the MD 200 taking place via a link 277, which may comprise a lead or, more preferably an inductive RF or similar wireless coupling. For example, in one embodiment, the heart parameter module 284 may be external to the medical device 200 and to the patient's body, e.g., in a monitoring unit 270. Locating the heart parameter module 284 in a monitoring unit 270 may be advantageous if the heart parameter calculation is computationally intensive, in order to reduce energy expenditure and heat generation in the MD 200 or to expedite calculation of the at least one heart parameter.

Monitoring unit 270 may be capable of displaying an indication to a patient that a heart parameter, such as an HRV parameter or a regulatory state parameter, has exceeded a threshold for that parameter. Monitoring unit 270 may also be capable of logging the time of the event, as well as initiate a severity determination to indicate the duration and extent of the heart parameter exceeding a threshold, and to notify a caregiver or store the information in one or more databases.

The monitoring unit 270 may be a device that is capable of programming electrical signal parameters of the MD 200. In one embodiment, the monitoring unit 270 is a computer system capable of executing a data-acquisition program. The monitoring unit 270 may be controlled by a healthcare provider, such as a physician, at a base station in, for example, a doctor's office. In alternative embodiments, the monitoring unit 270 may be controlled by a patient in a system providing less control over the operation of the MD 200 than another monitoring unit 270 controlled by a healthcare provider. Whether controlled by the patient or by a healthcare provider, the monitoring unit 270 may be a computer, preferably a handheld computer or PDA, but may alternatively comprise any other device that is capable of electronic communications and programming, e.g., hand-held computer system, a PC computer system, a laptop computer system, a server, a personal digital assistant (PDA), an Apple-based computer system, etc. The monitoring unit 270 may download various parameters and program software into the MD 200 for programming the operation of the IMD, and may also receive and upload various status conditions and other data from the MD 200. Communications between the monitoring unit 270 and the communication unit 260 in the MD 200 may occur via a wireless or other type of communication, represented generally by line 277 in FIG. 2. This may occur using, e.g., wand 155 (FIG. 1) to communicate by RF energy with implantable embodiments of MD 200, such as generator 110 (FIGS. 1A-C). Alternatively, the wand may be omitted in some systems, e.g., systems in which monitoring unit 270 operates in the MICS bandwidths.

In one embodiment, the monitoring unit 270 may comprise a local database unit 255. Optionally or alternatively, the monitoring unit 270 may also be coupled to a database unit 250, which may be separate from monitoring unit 270 (e.g., a centralized database wirelessly linked to a handheld monitoring unit 270). The database unit 250 and/or the local database unit 255 are capable of storing various patient data. This data may comprise patient heart beat and/or heart parameter data acquired from a patient's body, as well as therapy parameter data. The database unit 250 and/or the local database unit 255 may comprise data for a plurality of patients, and may be organized and stored in a variety of manners, such as in date format, severity of disease format, etc. The database unit 250 and/or the local database unit 255 may be relational databases in one embodiment. A physician may perform various patient management functions (e.g., programming parameters for a primary/chronic therapy and/or secondary/acute therapy modes) using the monitoring unit 270, which may include obtaining and/or analyzing data from the MD 200 and/or data from the database unit 250 and/or the local database unit 255. The database unit 250 and/or the local database unit 255 may store various patient data.

One or more of the blocks illustrated in the block diagram of the MD 200 in FIG. 2 may comprise hardware units, software units, firmware units, or any combination thereof. Additionally, one or more blocks illustrated in FIG. 2 may be combined with other blocks, which may represent circuit hardware units, software algorithms, etc. Additionally, any number of the circuitry or software units associated with the various blocks illustrated in FIG. 2 may be combined into a programmable device, such as a field programmable gate array, an ASIC device, etc.

The implantable medical device system of one embodiment of the present invention provides for software module(s) that are capable of acquiring, storing, and processing various forms of data, such as patient data/parameters (e.g., physiological data, side-effects data, such as heart rate, breathing rate, brain-activity parameters, disease progression or regression data, quality of life data, etc.) and therapy parameter data. Therapy parameters may include, but are not limited to, electrical signal parameters that define the therapeutic electrical signals delivered by the IMD, medication parameters and/or any other therapeutic treatment parameter. In an alternative embodiment, the term "therapy parameters" may refer to electrical signal parameters defining the therapeutic electrical signals delivered by the IMD. Therapy parameters for a therapeutic electrical signal may also include, but are not limited to, a current amplitude, a pulse width, a frequency, an on-time, an off-time, etc.

In one embodiment, the present invention may include coupling of at least one electrode to each of two or more cranial nerves. (In this context, two or more cranial nerves mean two or more nerves having different names or numerical designations, and do not refer to the left and right versions of a particular nerve). In one embodiment, at least one electrode may be coupled to either or both vagus nerves or a branch of either or both vagus nerves. The term "operatively" coupled may include directly or indirectly coupling. Each of the nerves in this embodiment or others involving two or more cranial nerves may be stimulated according to particular activation modalities that may be independent between the two nerves.

In one embodiment, the MD 200 may also be capable of detecting a manual input from the patient. The manual input may include a magnetic signal input, a tap input, a wireless data input to the MD 200, etc. In one embodiment, based upon the manual input, alterations in the treatment regimen may be provided for treating a chronic condition.

Turning now to FIG. 4A, a more detailed stylized depiction of the heart beat sensor interface 265 of FIG. 2, in accordance with one illustrative embodiment of the present invention is depicted. In one embodiment, the heart beat sensor interface 265 comprises a heart beat signal receiver 410, an analog-to-digital converter (A/D Converter) 420, and a heart beat data correlation unit 425. The heart beat signal receiver 410 is capable of receiving the signals from the sensor(s) 212. The signal that is received by the heart beat signal receiver 410 is then processed and filtered.

The heart beat signal receiver 410 may comprise a receiver circuit 412, amplifier(s) 414, and filter(s) 416. The receiver circuit 412 is capable of receiving input signal(s) from the sensor(s) 212. The receiver circuit 412 may be a multi-channel receiver that is capable of receiving a plurality of input signals from a plurality of channels. The receiver circuit 412 may comprise circuitry for receiving input signal, such as interface circuitry. The receiver circuit 412 may provide the input signal to the amplifier(s) 414. The amplifiers 414 are capable of buffering and amplifying the input signals received from the sensor(s) 212. The heart beat signal may be attenuated and may be characterized by significantly low amplitude responses and signal noise. The amplifier(s) 414 are capable of buffering (amplification by unity) and amplifying the signals for further processing. In one embodiment, the amplifier 414 may comprise op amp circuit(s), digital amplifier(s), buffer amplifiers, and/or the like.

The heart beat signal receiver 410 may also comprise one or more filters 416. The filters 416 may comprise analog filter(s), digital filter(s), filters implemented by digital signal processing (DSP) means or methods, etc. The amplified and buffered heart beat signal may be filtered to remove various noise signals residing on the heart beat signal. The filter 416, for example, is capable of filtering out various noise signals caused by external magnetic fields, electrical fields, noise resulting from physiological activity, etc. For example, signal noise due to breathing, or other signals produced by the patient's body may be filtered.

The heart beat signal receiver 410 is also capable of filtering various other signal components, such as performing an R-R interval rejection, wherein R-R beat components introduced to the heart beat signal may be corrected using this filter. Further, sampling-rate induced errors in the heart beat signal may be filtered using the filter 416. For example, a limited sampling rate may introduce an error into the heart rate variability (HRV) spectrum that may increase the frequency, particularly affecting higher frequency components. The filter 416 is capable of reducing or eliminating this effect.

The filter 416 may also be capable of performing an interpolation of the under-sampled ECG signal to decrease this error. Editing of R-R interval data may be performed on the heart beat signal. Certain R-R intervals may be eliminated to avoid unnecessary calculations. For example, R-R intervals that differ by more than a predetermined percentage, such as 20%, from the previous interval may be eliminated to maintain more accurate R-R interval signals, thereby performing the R-R data editing. The filter 416 may also perform artifact elimination due to various other components, such as breathing or other noise sources.

The heart beat signal receiver 410 provides amplified, filtered signals to the A/D converter 420. The A/D converter 420 performs an analog-to-digital conversion for further processing of the heart beat signal. The A/D converter 420 may be one type of a plurality of converter types with various accuracies, such as an 8-bit converter, a 12-bit converter, a 24-bit converter, a 32-bit converter, a 64-bit converter, a 128-bit converter, a 256-bit converter, etc. The converted digital signal is then provided to a heart beat data correlation unit 425. In an alternative embodiment, the A/D conversion may be performed prior to filtering or signal processing of the heart beat signal. The converted digital signal is then provided to a heart beat data correlation unit 425.

The heart beat data correlation unit 425 is capable of organizing, correlating, stacking, and otherwise processing the digitized, buffered, and filtered heart beat data. The heart beat correlation unit 425 is capable of correlating and organizing the digitized heart beat signal. The correlation unit 425 may correlate various time stamps with the heart beat signal to provide a time of beat sequence of the patient's heart. Further, the heart beat data correlation unit 425 is capable of correlating various physiological events to the heart beat data. The digital signals issuing from the heart beat data correlation unit 425 may then be forwarded to the heart beat data processing module 275.

Turning now to FIG. 4B, a more detailed stylized depiction of the heart beat data processing module 275 of FIG. 2, in accordance with one illustrative embodiment of the present invention is depicted. The heart beat data processing module 275 may comprise a heart beat determination module 430, a beat interval determination module 440, a beat interval time series storage unit 450, and a beat interval statistics module 460. The heart beat data processing module 275 may determine heart beats as they appear in the time series of signals via the heart beat determination module 430. For example, heart beat determination module 430 may characterize certain data points in the time series of signals as corresponding to the start, the peak, or the end of an R-wave of a patient's cardiac cycle.

Once heart beats are determined from the time series of signals, the beat interval determination module 440 may determine the interval between consecutive beats ("beat interval") and forward this information to beat interval time series storage 450. From the determined beat interval and/or the time series thereof, the beat interval statistics module 460 can determine various statistical values of the beat interval time series, e.g., mean, median, or standard deviation, among others, for various timescales (e.g., 5 minutes, 1 hour, 24 hours). The beat interval time series, the statistical values thereof, or both may be used for further processing.

Figure 5A:
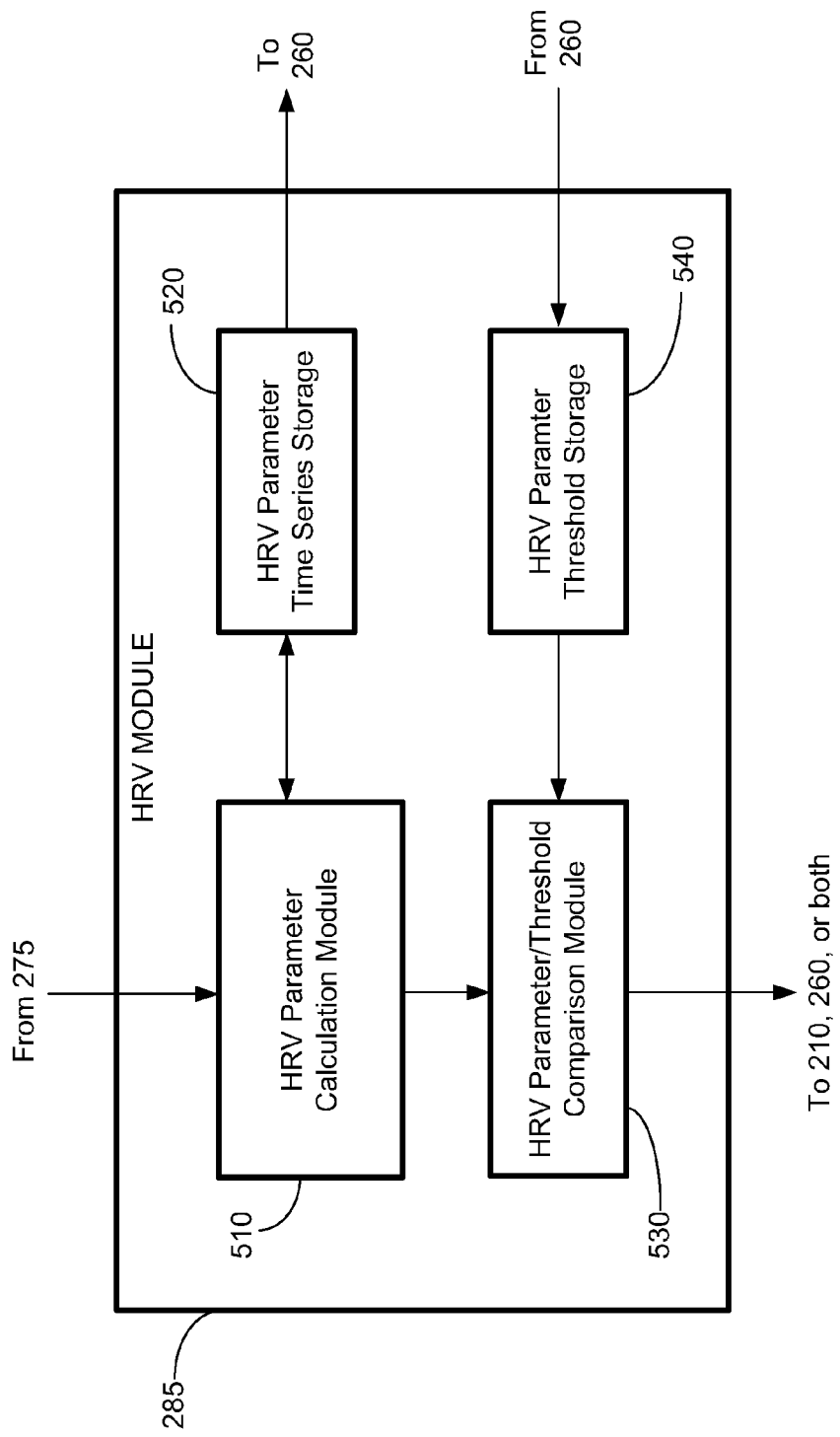
FIG. 5A illustrates a block diagram of a heart rate variability (HRV) module of the implantable medical device, in accordance with one illustrative embodiment of the present invention.

Turning now to FIG. 5A, a more detailed stylized depiction of the HRV module 285 within heart parameter module 284 of FIG. 2, in accordance with one illustrative embodiment of the present invention is depicted. The HRV module 285 may receive various data from the heart beat data processing module 275. Based upon data from the heart beat data processing module 275, the HRV module 285 is capable of determining at least one HRV parameter that is associated with a parasympathetic function of the patient, and performing further calculations in light of the HRV parameter, which may lead it to provide information to the controller 210. In one embodiment, the HRV module 285 is capable of determining that a treatment should be provided to treat a chronic or non-episodic disorder. This indication may be stored internally and/or externally, e.g., in the memory 217 (FIG. 2). This indication may also be transmitted to a separate device, e.g., to the monitoring unit 270 and/or stored, e.g., into the local database unit 255 and/or the database unit 250 (FIG. 2). Heart module 284 and/or HRV module 285 may initiate other responsive actions such as providing an audible, visible, or tactile alert to the patient or a caregiver; logging a timestamp of the determination of a need for treating the chronic medical condition; initiation of a severity determination routine based upon data from the heart beat data processing module 275 and/or the HRV module 285 itself, communicating with one or more of database unit 250 or remote device 292, or notifying emergency services via email, autophone communications, wireless communications, etc. It may be appreciated that, based upon the output of the heart parameter module 284, responsive action(s) may be performed by either the MD 200, monitoring unit 270, or other devices such as remote device 292.

The beat interval time series, its statistical values, or both are analyzed by an HRV parameter calculation module 510, which determines the value of the at least one HRV parameter of interest. The HRV parameter calculation module 510 may store results in HRV parameter time series storage 520, which may be a portion of the memory 217 or a separate memory unit. The HRV parameter calculation module 510 may also access information from HRV parameter time series storage 520 to calculate one or more HRV parameters. The HRV parameter time series storage 520 may communicate HRV parameter time series information to a monitoring unit 270 via communications unit 260.

After calculating the at least one HRV parameter of interest (module 510), the calculated value may be compared to a threshold value by an HRV parameter/threshold comparison module 530. The threshold value used by the module 530 may be stored in HRV parameter threshold storage 540 after being placed there by a physician via communications unit 260. The threshold value used by the module 530 may be a portion of the memory 217 or a separate memory unit. In one embodiment, the HRV parameter threshold storage module 540 may calculate a threshold value to provide an adaptive threshold rather than a fixed threshold. For example, thresholds may be calculated from a baseline HRV value for a particular patient that is determined from data stored in HRV parameter time series storage 520, or other algorithms for determining a threshold may be implemented. In another embodiment, an HRV parameter threshold may be modified based upon circadian rhythms of the patient.

Figure 5B:
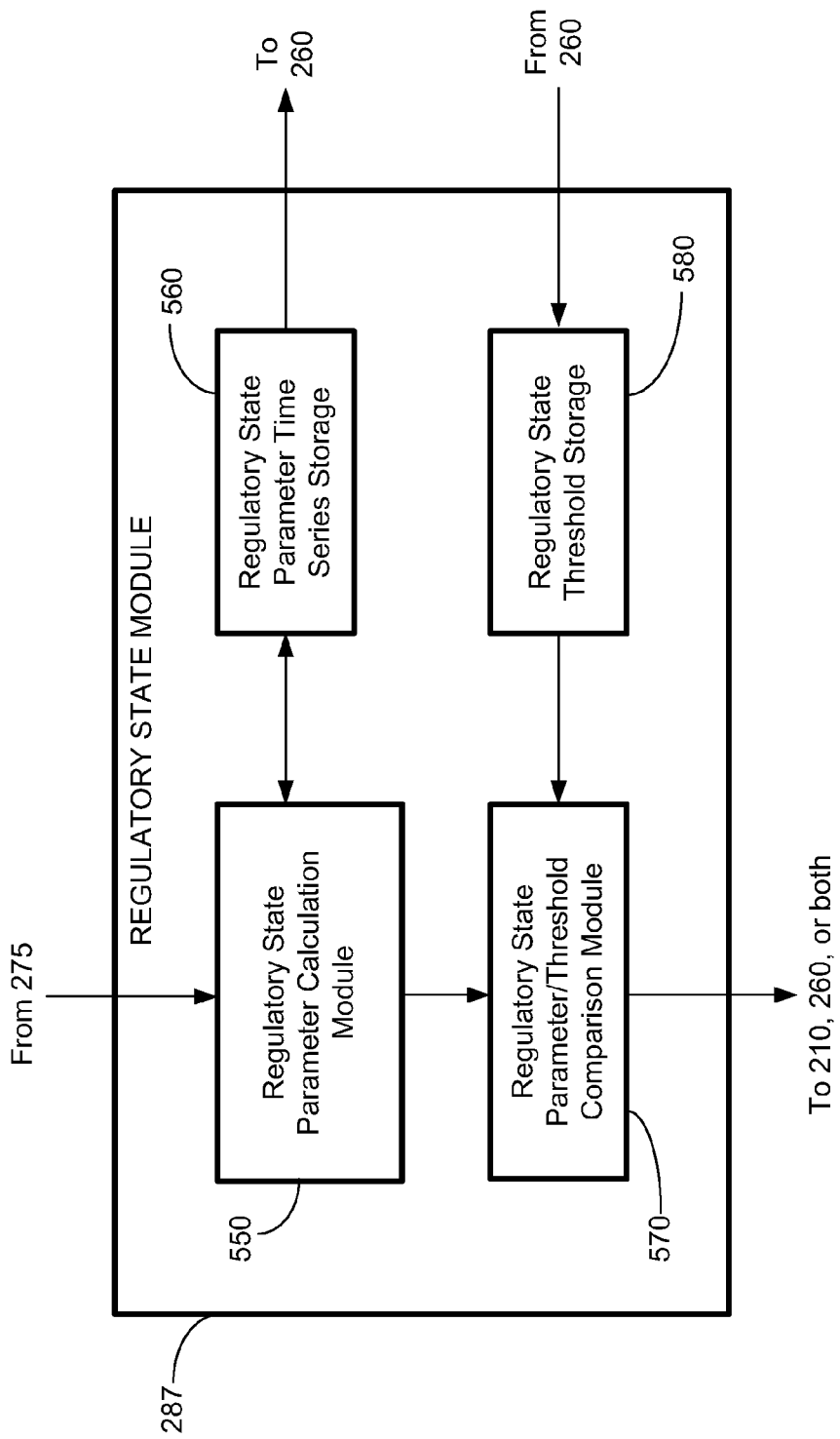
FIG. 5B illustrates a block diagram of a regulatory state module of the implantable medical device, in accordance with one illustrative embodiment of the present invention.

Turning now to FIG. 5B, a more detailed stylized depiction of the regulatory state module 287 of FIG. 2, in accordance with one illustrative embodiment of the present invention is depicted. The regulatory state module 287 may receive various data from the heart beat data processing module 275.

Based upon data from the heart beat data processing module 275, the regulatory state module 287 is capable of determining at least one regulatory state parameter, such as those described above (e.g., IARS), and performing further calculations in light of the regulatory state parameter, which may lead it to provide information to the controller 210. In one embodiment, the regulatory state module 287 is capable of determining that a treatment should be provided to treat a chronic or non-episodic disorder. This indication may be stored internally and/or externally, e.g., in the memory 217 (FIG. 2). This indication may also be transmitted to an external entity, e.g., to the monitoring unit 270 and/or stored, e.g., into the local database unit 255 and/or the database unit 250 (FIG. 2). Module 287 may also initiate other responsive actions such as those described for HRV module 285 in FIG. 5A, supra.

The beat interval time series, its statistical values, or both are analyzed by a regulatory state parameter calculation module 550, which determines the value of the at least one regulatory state parameter of interest. The regulatory state calculation module 550 may store results in regulatory state parameter time series storage 560, which may be a portion of the memory 217 or a separate memory unit. The regulatory state parameter calculation module 550 may also access information from regulatory state parameter time series storage 560 to calculate one or more regulatory state parameters. The regulatory state parameter time series storage 560 may communicate regulatory state parameter time series information to a monitoring unit 270 via communications unit 260.

After module 550 calculates the at least one regulatory state parameter of interest, the value may be compared to a threshold value by a regulatory state parameter/threshold comparison module 570. The threshold value used by the module 570 may be stored in a regulatory state threshold storage 580 after being placed there by a physician via communications unit 260. The threshold value used by the module 570 may be a portion of the memory 217 or a separate memory unit. As with the HRV threshold value, module 580 may also calculate an adaptive threshold rather than a fixed threshold, based upon a baseline regulatory state parameter, environmental or patient-specific parameters, or combinations of the foregoing.

Figure 6:
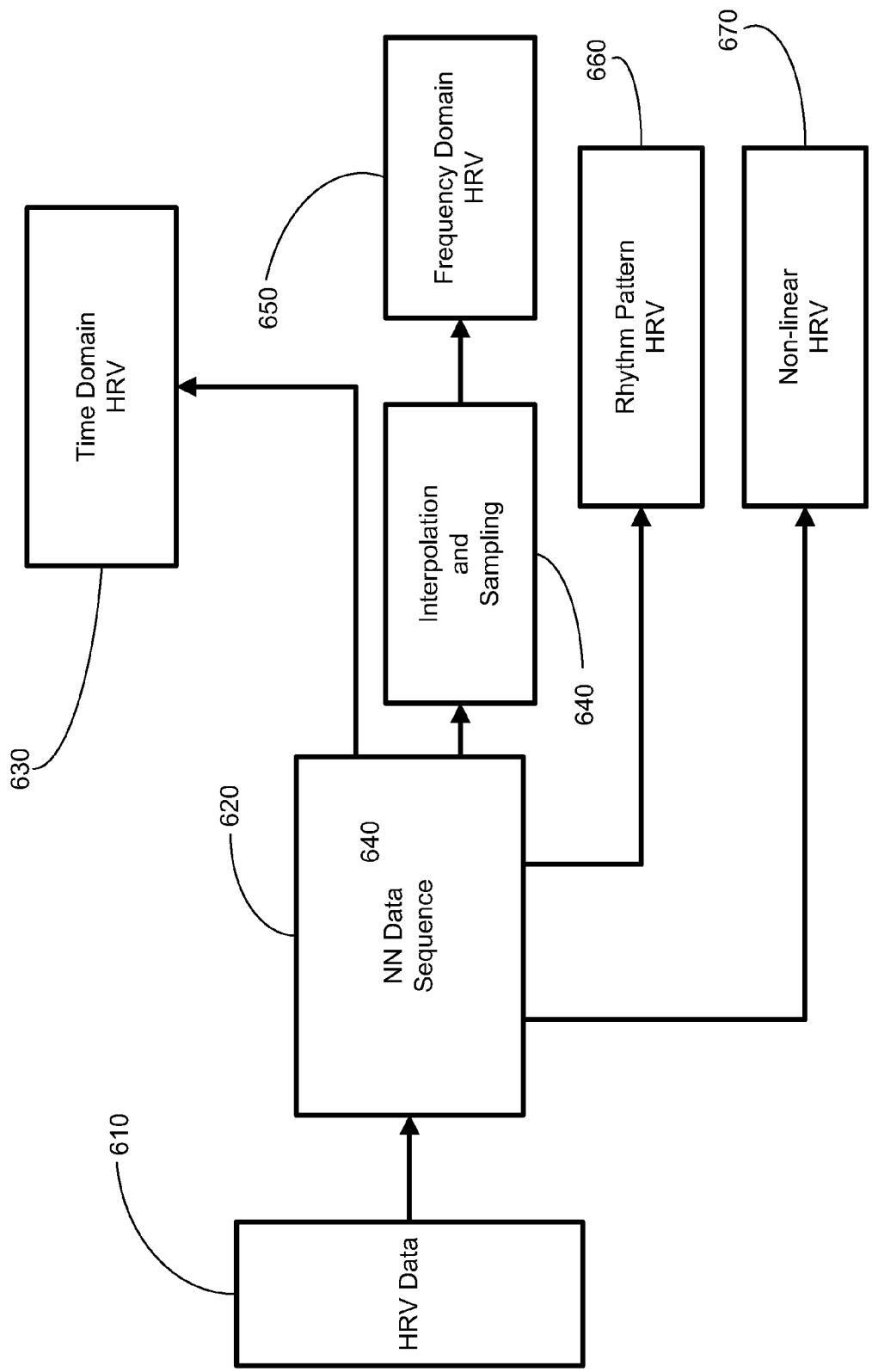
FIG. 6 illustrates a flowchart relating to a function performed by a heart beat data processing module of FIG. 2, in accordance with one illustrative embodiment of the present invention.

Turning now to FIG. 6, a flowchart depiction of steps involving processing heart rate variability (HRV) data, in accordance with one illustrative embodiment of the present invention, is provided. Heart beat data is received by the MD 200 (block 610). In one embodiment, HRV data is used to determine an NN data sequence. In one embodiment, the variations in heart beat data may be evaluated based upon time domain analysis (block 630). In another embodiment, the variations in heart beat data may be evaluated based upon a frequency domain analysis (block 650). In still other embodiments, the variations in heart beat data may be subjected to rhythm pattern analysis (block 660) and/or nonlinear HRV analysis (block 670).

Based upon data from an ECG, the QRS complex may be evaluated. Based upon the QRS complex, normal-to-normal (NN) intervals may be determined (block 620). As noted above, NN intervals may refer to intervals between adjacent corresponding QRS complexes. Time domain variables may then be calculated based upon the NN intervals (block 630). Examples of the time domain variables may include mean NN intervals, instantaneous heart rate, the difference between the longest and shortest NN intervals, the difference between heart rate for different time periods, etc. Direct measurements of the NN intervals, instantaneous heart rate, or NN determination based upon differences between the intervals may be analyzed. A standard deviation of the NN intervals may be made to provide a standard deviation NN parameter (SDNN), which may reflect cyclic components relating to the variability in the heart rate signals for a given time period. The SDNN is an example of a statistical parameter.

The NN data sequence is used to perform the time domain analysis of the HRV to provide various parameters that may be indicative of a patient's regulatory system. The NN data sequence may also be used to perform interpolation and data sampling to perform a frequency domain analysis of the HRV (block 640). A spectral method, such as a power spectral density (TSD) analysis may provide information relating to the power (variance) distribution as a function of frequency. Algorithms, such as fast Fourier transform (FFT) may be performed for such analysis. Parameters such as total power for a particular time period may be calculated to provide an indication of the variance of the NN intervals over a time period. The HRV signals may be analyzed to provide a calculation of low frequency (LF) and high frequency (HF) power components with emphasis upon a central frequency of each component. Based on the time domain HRV analysis and/or the frequency domain HRV analysis, various indications of heart rate variability parameters for detecting regulatory system operation of the patient is possible. The HRV analysis of the patient's regulatory system includes one or more of a statistical parameter, a spectral parameter, a fractal parameter, and/or a non-linear parameter. Examples of statistical parameter may include the SDNN, the SDANN, the RMSSD, and PNN50, among others. Examples of the spectral parameter may be an LF power, an HF power, and/or a ratio thereof, among others. Examples of a non-linear parameter may be a Lyapunov exponent or a Kolmogorov exponent, as described above, among others.

Figure 7:
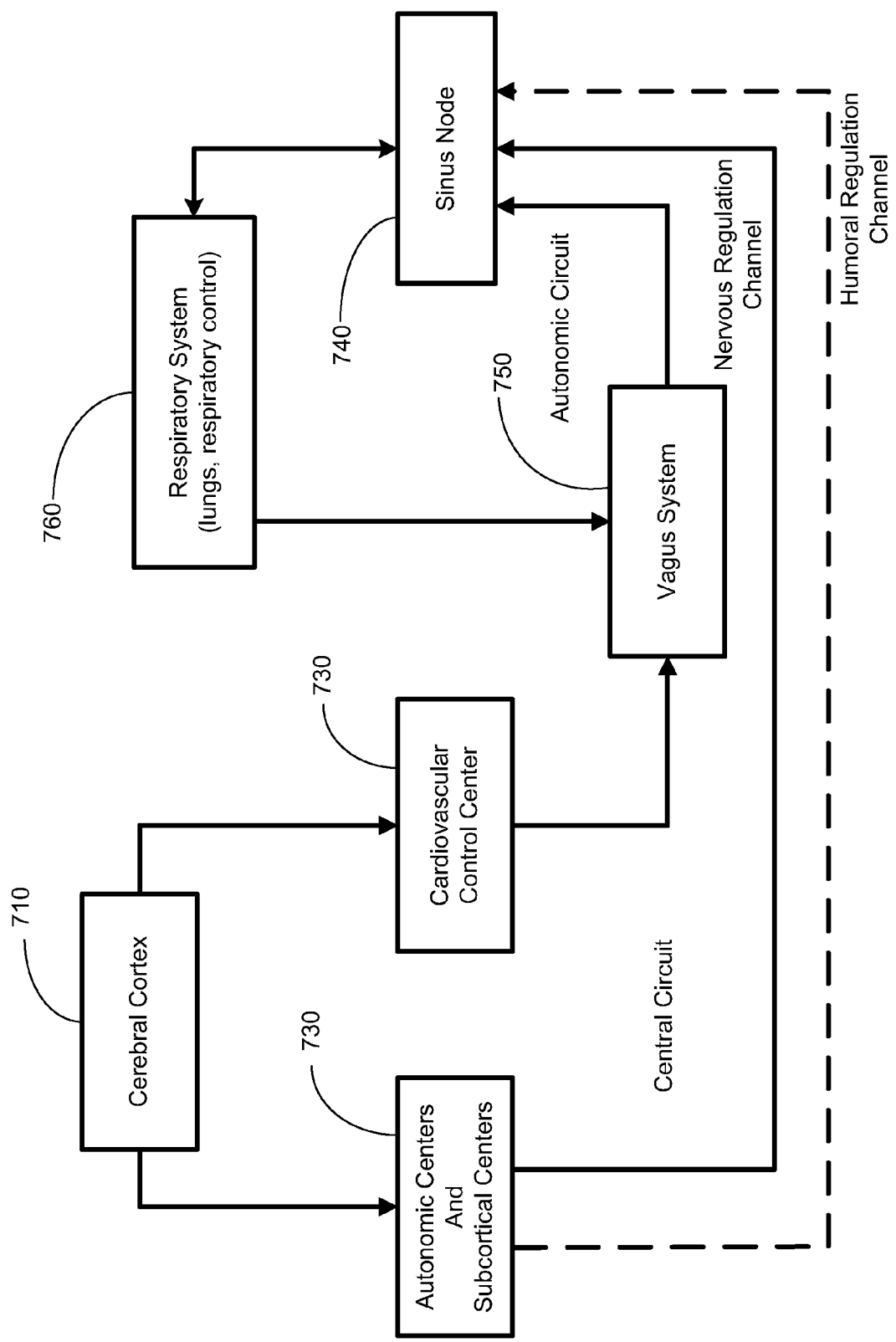
FIG. 7 illustrates a block diagram depiction of a heart rhythm regulation module, in accordance with one illustrative embodiment of the present invention.

Turning now to FIG. 7, a circuit type model of the parasympathetic interaction with the heart rhythm is illustrated. As noted above, HRV data may be viewed as relating to one or more regulatory mechanisms influencing the circulatory system of a patient. As illustrated in FIG. 7, the cerebral cortex (block 710) interfaces with the autonomic centers and the subcortical nerve centers (block 720) and with the cardiovascular control center (block 730) in the medulla oblongata. Blocks 720-730 make up the central circuit of the regulation of the heart beat, which is controlled by the neurohumoral regulation of the physiological functions.

FIG. 7 also illustrates an autonomic circuit, which may include the sinus node 740 and the vagus system (block 750), which includes the vagus nuclei in the medulla oblongata. The autonomic circuit also includes a feedback component, i.e., the respiratory system (block 760) which includes the lungs and the respiratory control center. A connection between the central circuit and the autonomic circuit may be provided by the nervous regulation channel.

Stress upon the system of FIG. 7 may be exacerbated by a chronic medical condition, and may be characterized using the disclosures of the present application. This characterization may be used as a triggering mechanism to provide improved treatment methods for chronic conditions. Certain chronic disorders may affect, and be affected by, the parasympathetic activity of the body. The HRV parameters exemplified herein may be used as a triggering mechanism for aiding a determination whether to treat the chronic conditions that cause adverse effects upon the parasympathetic system of the patient's body. For example, a therapeutic stimulation signal may be applied to a portion of the vagus system (e.g., a portion of the vagus nerve) to affect a patient's parasympathetic system, which may thereby affect the interaction between the autonomic circuit and the central circuit, and their respective functions. This modulation of the parasympathetic system may result in treatment of a chronic or non-episodic condition or disorder. By providing treatment in response to detection of HRV or regulatory system parameters exceeding acceptable thresholds, it is believed that improved treatments for the chronic medical condition may be provided.

Figure 8:
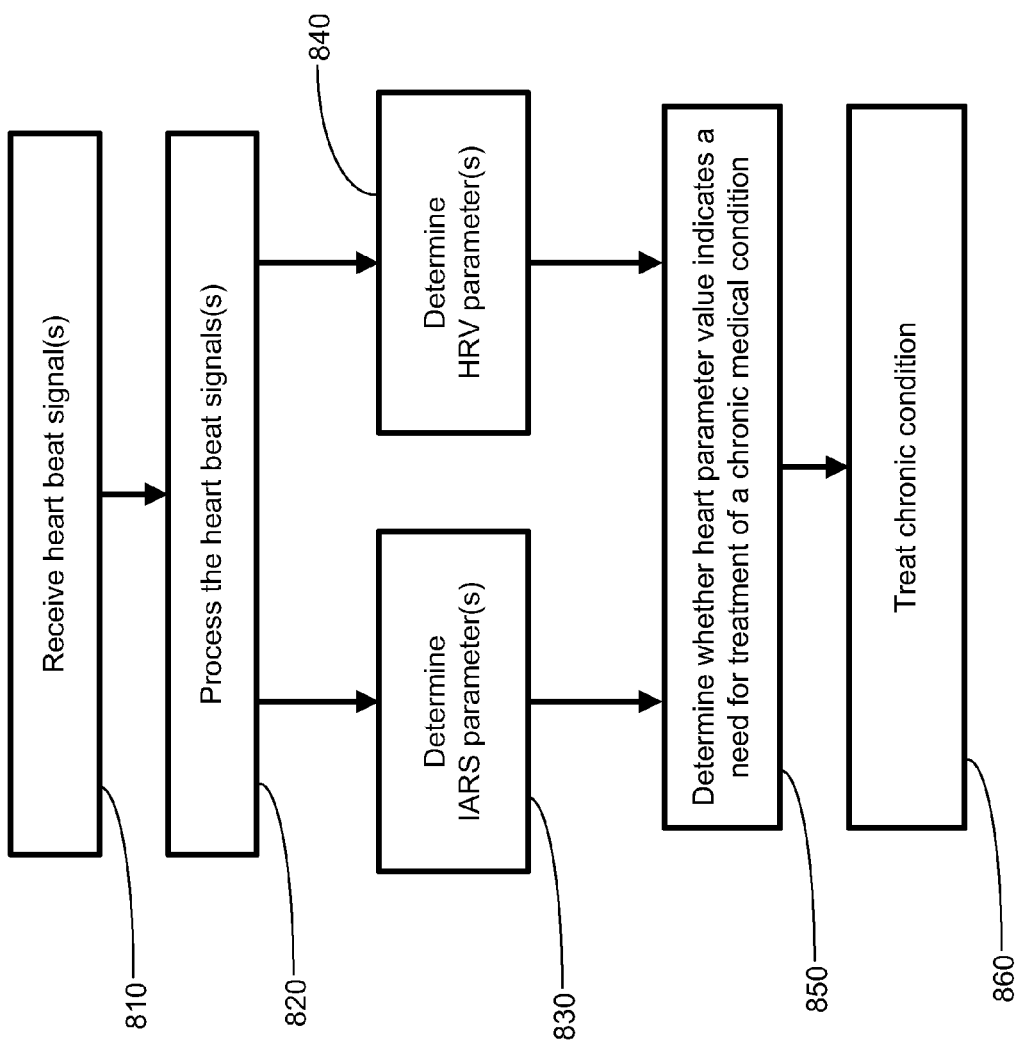
FIG. 8 illustrates a flowchart depiction of steps for treating a chronic medical condition using a medical device, in accordance with one illustrative embodiment of the present invention.

Turning now to FIG. 8, a stylized flowchart depiction of providing treatment of a chronic medical condition by the MD 200, in accordance with one illustrative embodiment of the present invention, is provided. The MD 200 receives a heart beat signal (block 810). The heart beat sensor interface 265 in the MD 200 receives the heart beat signal. After performing buffering, amplification, filtering, and A/D conversion of the heart beat signal, the heart beat data processing module 275 processes the heart beat data for performing analysis of heart beat data (block 820). The processing of the heart beat data may be performed by the heart beat data processing module 275 (FIG. 2).

Based upon the processed HRV data, a step for determining an IARS parameter (block 830) and/or at least one HRV parameter (block 840) are determined. As noted above, the determination of the regulatory parameter or the HRV parameter(s) of the patient may be analyzed. In particular, an IARS (regulatory) parameter or any of numerous HRV parameters (e.g., a statistical parameter, a spectral parameter, and/or a non-linear parameter) may be determined. Based upon the parameters that relate to the regulatory system of the patient, a determination may be made as to whether the regulatory and/or HRV parameter(s) indicate a need for treatment of a chronic medical condition of the patient. (block 850). Some embodiments of the present invention are directed to treating chronic conditions that adversely affect the patient's parasympathetic system. Accordingly, the relationship between the chronic medical condition and the parasympathetic system of the patient may be determined. A more detailed description of the steps for determining whether the regulatory and/or HRV parameters indicate a need for treatment (block 850) is further described in FIGS. 8 and 9 and accompanying description below.

Upon determining that the regulatory and/or HRV parameter(s) indicates a need for treatment of the chronic condition, the MD 200 may then treat the chronic condition (block 860). This treatment may include providing an electrical signal therapy to a portion of the vagus nerve to affect the parasympathetic system of the patient's body.

Figure 9:
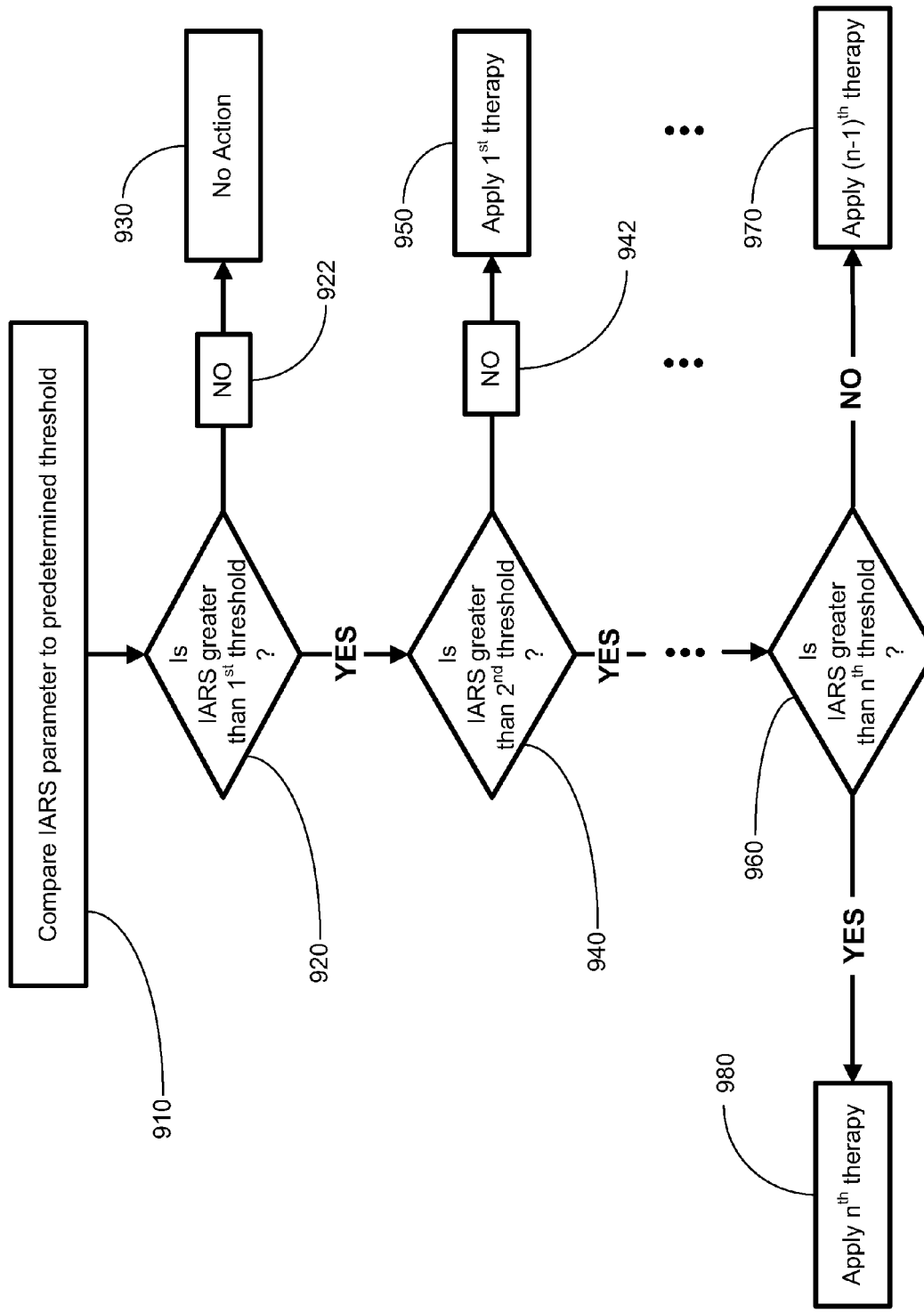
FIG. 9 illustrates a flowchart depiction of treating a chronic condition using an IARS parameter, in accordance with one illustrative embodiment of the present invention.

Referring now to FIG. 9, an algorithm is provided to illustrate how a determined IARS parameter (i.e., a regulatory parameter) may be used to determine whether a chronic medical condition of a patient should be treated. A comparison of the determined IARS parameter to a first threshold IARS value may be performed (block 910). A determination is made whether the determined IARS value is greater than a first IARS threshold value (block 920). In the event that a determination is made that the determined IARS value is not greater than the first IARS threshold value (block 922), no application of therapy is performed at that time (blocks 930).

In a similar manner, a determination may be made whether the IARS is greater than a second IARS threshold (block 940). If the IARS parameter is not greater than the second threshold (block 942), then a first therapy is applied (e.g., an electrical signal therapy applied to a vagus nerve) to the patient (block 950). In this manner, if the IARS is greater than the first IARS threshold, but not greater than the second IARS threshold, a first therapy signal is applied. This process may be repeated numerous times wherein a comparison is made whether the IARS is greater than an $n^{th}$ IARS threshold (block 960). Upon a determination that the IARS parameter is not greater than the $n^{th}$ threshold, an $(n-1)^{th}$ therapy signal (e.g., an electrical signal applied to a vagus nerve) is applied to the patient (block 970). However, if the IARS parameter is greater than or equal to the $n^{th}$ threshold, then the $n^{th}$ therapy is applied (block 980). In this manner, depending on the value of the IARS parameter, one of a number of electrical signal therapies may be applied. Therefore, depending on the stress, tension, instability, or complete exhaustion of the regulatory system of the patient, particular therapies or interventions may be applied to treat the patient's chronic medical condition.

Figure 10:
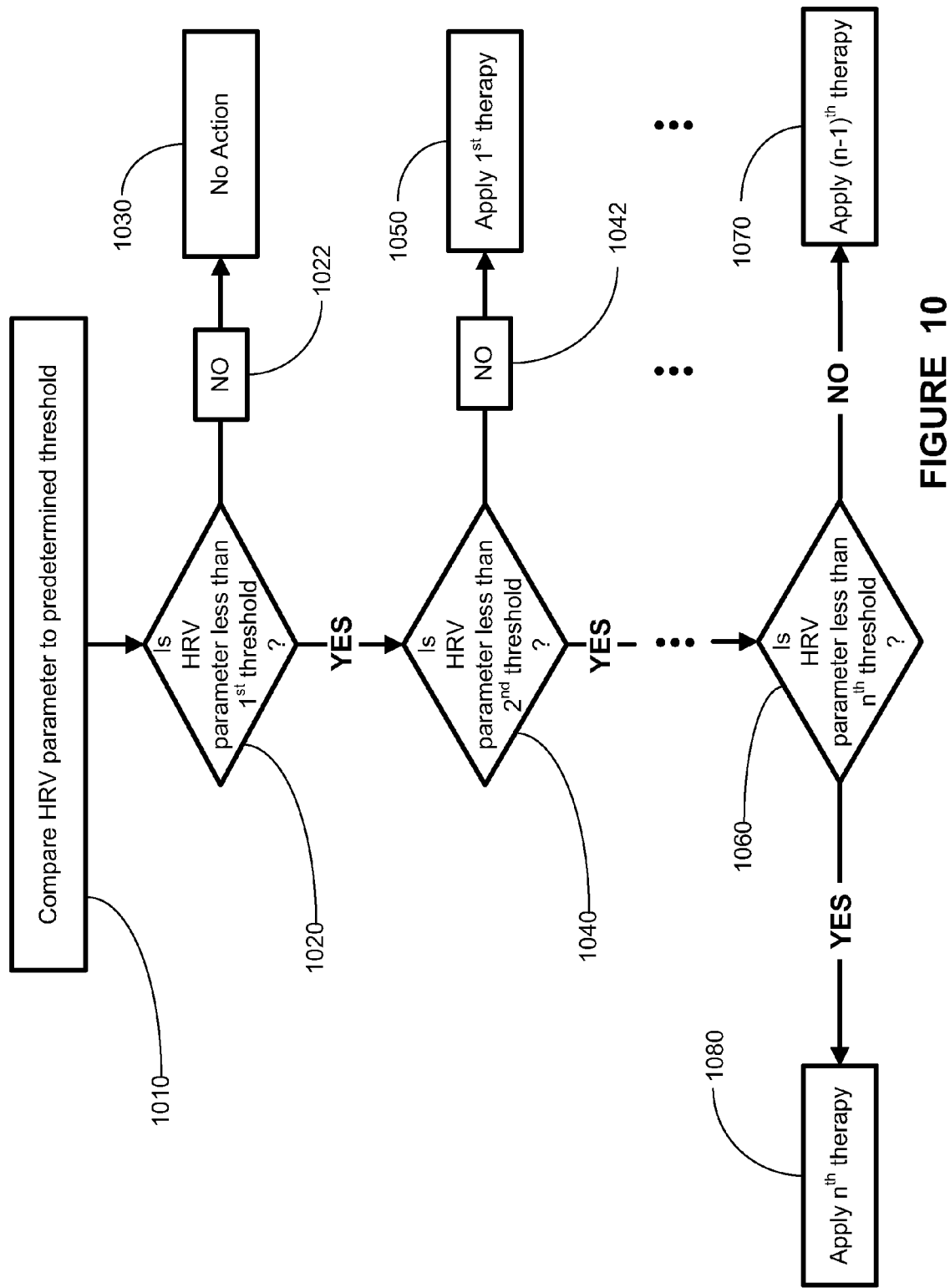
FIG. 10 illustrates a flowchart depiction of treating a chronic condition using an HRV parameter in accordance with one illustrative embodiment of the present invention.

Referring now to FIG. 10, an algorithm is provided to illustrate how a determined HRV parameter may be used to determine whether a chronic medical condition of a patient should be treated. A comparison of a determined HRV parameter to a first predetermined threshold HRV parameter value may also be performed (block 1010). A determination is made as to whether a determined HRV parameter is less than a first threshold HRV parameter value (block 1020). In the event that a determination is made that the determined HRV parameter value is not greater than the first threshold HRV parameter value (block 1022), no application of therapy is performed at that time (blocks 1030).

Similarly, a determination may be made as to whether the determined HRV parameter value is less than a second HRV threshold value (block 1040). If the HRV parameter is not less than the second HRV parameter threshold (block 1042), then a first therapy is applied to the patient (block 1050). In this manner, if the HRV parameter is less than the first HRV threshold, but not less than the second HRV threshold, a first therapy signal is applied. This process may be repeated numerous times wherein a comparison is made whether the HRV is less than an $n^{th}$ HRV threshold (block 1060). Upon a determination that the HRV parameter is not less than the $n^{th}$ threshold, an $(n-1)^{th}$ therapy signal is applied to a portion of a cranial nerve (e.g., vagus nerve) of the patient (block 1070). However, if the HRV parameter is less than or equal to the $n^{th}$ threshold, then the $n^{th}$ therapy is applied (block 1080). In this manner, depending on the value of the HRV parameter, one of a number of electrical signal therapies may be applied. Therefore, depending on the stress, tension, or instability of the regulatory system of the patient, particular therapy signals may be applied to treat a chronic medical condition. Utilizing the techniques described herein, various types of chronic conditions or non-episodic conditions may be treated.

All of the methods and apparatuses disclosed and claimed herein may be made and executed without undue experimentation in light of the present disclosure. While the methods and apparatus of this invention have been described in terms of particular embodiments, it will be apparent to those skilled in the art that variations may be applied to the methods and apparatus and in the steps, or in the sequence of steps, of the method described herein without departing from the concept, spirit, and scope of the invention, as defined by the appended claims. It should be especially apparent that the principles of the invention may be applied to selected cranial nerves other than, or in addition to, the vagus nerve to achieve particular results in treating patients having epilepsy, depression, or other medical conditions.

The particular embodiments disclosed above are illustrative only as the invention may be modified and practiced in different but equivalent manners apparent to those skilled in the art having the benefit of the teachings herein. Furthermore, no limitations are intended to the details of construction or design herein shown other than as described in the claims below. It is, therefore, evident that the particular embodiments disclosed above may be altered or modified and all such variations are considered within the scope and spirit of the invention. Accordingly, the protection sought herein is as set forth in the claims below.

What is claimed:

1. A method of adapting treatment of a patient having a chronic medical condition during periods of heightened stress on regulatory adaptation systems of the patient, comprising:
    applying a first electrical signal to a neural structure of the patient to treat the chronic medical condition, the first electrical signal defined by a first set of signal parameter values;
    determining a time of beat sequence of the patient's heart;
    determining a first index of activity of regulatory systems (IARS) value based on said time of beat sequence, the first IARS value indicative of a stress level of the regulatory adaptation systems of the patient;
    comparing the first IARS value to a first IARS threshold; and
    adjusting the first electrical signal to provide a second electrical signal to the neural structure of the patient in response to the first IARS value exceeding the first IARS threshold, the second electrical signal defined by a second set of signal parameter values, wherein at least one value of the second set of signal parameter values is different from a corresponding value in the first set of signal parameter values.

2. The method of claim 1, wherein the first IARS threshold is an adaptive threshold that changes in response to at least one factor selected from among a circadian rhythm of the patient, a time of day, a cardiac parameter other than IARS derived from said time of beat sequence, a blood parameter measured for the patient, a health status of the patient, and a baseline IARS value for the patient.

3. The method of claim 1, wherein the neural structure comprises at least one neural structure selected from among a brain structure of the patient, a cranial nerve of the patient, a spinal cord of the patient, a sympathetic nerve structure of the patient, and a peripheral nerve of the patient.

4. The method of claim 1, wherein the chronic medical condition comprises at least one chronic medical condition selected from among traumatic brain injury; complications from stroke; chronic cardiac disorders (including congestive heart failure); obesity; a neuropsychiatric disorder selected from the group consisting of schizophrenia, depression, and borderline personality disorder; multiple sclerosis; fibromyalgia; and arthritis.

5. The method of claim 1, further comprising:
    comparing the first IARS value to a second threshold IARS value in response to determining that the first IARS value exceeds the first threshold IARS value; and
    adjusting the first electrical signal to provide a third electrical signal to the neural structure of the patient in response to the first IARS value exceeding the second threshold IARS value, the third electrical signal defined by a third set of signal parameter values, wherein at least one value of the third set of signal parameter values is different from a corresponding value in the first set of signal parameter values and the second set of signal parameter values.

6. The method of claim 1, further comprising:
    determining a second IARS value for said patient after providing the second electrical signal to the neural structure of the patient;
    comparing the second IARS value to the first threshold IARS value;
    adjusting the second electrical signal to provide the first electrical signal to the neural structure of the patient in response to the second IARS value being less than or equal to the first threshold IARS value.

7. The method of claim 1, further comprising:
    calculating a first baseline IARS value for the patient having the chronic medical condition.

8. The method of claim 7, further comprising:
    determining the first threshold IARS value based on the first baseline IARS value.

9. The method of claim 8, further comprising:
    modifying the first baseline IARS value to provide a second baseline IARS value based on a change in an environmental parameter, a patient-specific parameter, or a combination thereof; and
    adjusting the first threshold IARS value to provide a new first threshold IARS value based on the second baseline IARS value.

10. The method of claim 1, wherein the at least one value of the second set of signal parameter values that is different from a corresponding value in the first set of signal parameter values is for at least one corresponding parameter selected from among a current amplitude, a pulse-width, a frequency, an on-time, and an off-time.

11. A non-transitory computer readable program storage device encoded with instructions that, when executed by a computer, performs a method of adapting treatment of a patient having a chronic medical condition during periods of heightened stress on regulatory adaptation systems of the patient, the method comprising:
    providing a first electrical signal to a neural structure of the patient to treat the chronic medical condition, the first electrical signal defined by a first set of signal parameter values;
    determining a time of beat sequence of the patient's heart;
    determining a first index of regulatory activity systems (IARS) value associated with the patient based upon the time of beat sequence;
    comparing the first IARS value to a first threshold IARS value;
    comparing the first IARS value to a second threshold IARS value in response to determining that the first IARS value exceeds the first threshold IARS value; and
    adjusting the first electrical signal to provide a second electrical signal to the neural structure of the patient in response to the first IARS value exceeding the first threshold IARS value and not exceeding the second threshold IARS value, the second electrical signal defined by a second set of signal parameter values, wherein at least one value of the second set of signal parameter values is different from a corresponding value in the first set of signal parameter values.

12. The non-transitory computer readable program storage device encoded with instructions that, when executed by a computer, performs the method of claim 11, further comprising:
    adjusting the first electrical signal to provide a third electrical signal to the neural structure of the patient in response to the first IARS value exceeding the second threshold IARS value, the third electrical signal defined by a third set of signal parameter values, wherein at least one value of the third set of signal parameter values is different from a corresponding value in the first set of signal parameter values and the second set of signal parameter values.

13. The non-transitory computer readable program storage device encoded with instructions that, when executed by a computer, performs the method of claim 11, further comprising:
  determining a second IARS value for said patient after providing the second electrical signal to the neural structure of the patient;
  comparing the second IARS value to the first threshold IARS value; and
  adjusting the second electrical signal to provide the first electrical signal to the neural structure of the patient in response to the second IARS value being less than or equal to the first threshold IARS value.

14. The non-transitory computer readable program storage device encoded with instructions that, when executed by a computer, performs the method of claim 11, wherein the chronic medical condition is at least one condition selected from among a traumatic brain injury; complications from stroke; a chronic cardiac disorder; obesity; a neuropsychiatric disorder selected from the group consisting of schizophrenia, depression, and borderline personality disorder; multiple sclerosis; fibromyalgia; and arthritis.

15. A method adapting treatment of a patient having a chronic medical condition during periods of heightened stress on regulatory adaptation systems of the patient, the chronic medical condition being selected from among traumatic brain injury, depression, and fibromyalgia, the method comprising:
  applying a first electrical signal to a cranial nerve of the patient to treat the chronic medical condition, the first electrical signal defined by a first set of signal parameter values;
  determining a time of beat sequence of the patient's heart by sensing the time of beat sequence of the patient's heart and processing the data relating to the beat sequence to generate a time series data stream from said time of beat sequence;
  determining a first index of activity of regulatory systems (IARS) value based on said time of beat sequence, wherein said value is indicative of a stress level of the regulatory adaptation systems of the patient;
  comparing said determined first IARS value with a first threshold IARS value; and
  adjusting the first electrical signal to provide a second electrical signal to the cranial nerve of the patient to treat the chronic medical condition in response to the first IARS value exceeding the first threshold IARS value, the second electrical signal defined by a second set of signal parameter values, wherein at least one value of the second set of signal parameter values is different from a corresponding value in the first set of signal parameter values.

16. The method of claim 15, wherein the first threshold IARS value is an adaptive threshold that changes in response to at least one factor selected from among a circadian rhythm of the patient, a time of day, a cardiac parameter other than IARS derived from said time of beat sequence, a blood parameter measured for the patient, a health status of the patient, and a baseline IARS value for the patient.

17. The method of claim 15, further comprising:
  comparing the first IARS value to a second threshold IARS value in response to determining that the second IARS value exceeds the first threshold IARS value; and
  adjusting the first electrical signal to provide a third electrical signal to the cranial nerve of the patient in response to the first IARS value exceeding the second threshold IARS value, the third electrical signal defined by a third set of signal parameter values, wherein at least one value of the third set of signal parameter values is different from a corresponding value in the first set of signal parameter values and the second set of signal parameter values.

18. The method of claim 15, further comprising:
  determining a second IARS value for said patient after providing the second electrical signal to the cranial nerve of the patient;
  comparing the second IARS value to the first threshold IARS value; and
  adjusting the second electrical signal to provide the first electrical signal to the cranial nerve of the patient in response to the second IARS value being less than or equal to the first threshold IARS value.

19. The method of claim 15, further comprising:
  calculating a first baseline IARS value for the patient having the chronic medical condition;
  determining the first threshold IARS value based on the first baseline IARS value;
  recalculating the first baseline IARS value to provide a second baseline IARS value for the patient, the second baseline IARS value different from the first baseline IARS value; and
  adjusting the first threshold IARS value to provide a new first threshold IARS value based on the second baseline IARS value.

20. The method of claim 19, further comprising:
  determining the first threshold IARS value based on the first baseline IARS value.

21. The method of claim 20, further comprising:
  modifying the first baseline IARS value to provide a second baseline IARS value based on a change in an environmental parameter, a patient-specific parameter, or a combination thereof; and
  adjusting the first threshold IARS value to provide a new first threshold IARS value based on the second baseline IARS value.

22. The method of claim 15, wherein the at least one value of the second set of signal parameter values that is different from a corresponding value in the first set of signal parameter values is for at least one corresponding parameter selected from among a current amplitude, a pulse-width, a frequency, an on-time, and an off-time.

23. A medical device for adapting treatment of a patient having a chronic medical condition during periods of heightened stress on regulatory adaptation systems of the patient, comprising:
  an electrical signal module configured to apply a first electrical signal to a neural structure of the patient to treat the chronic medical condition, the first electrical signal defined by a first set of signal parameter values;
  a heart beat data processing module configured to determine a time of beat sequence of the patient's heart;
  a heart parameter module configured to determine an index of activity of regulatory systems (IARS) value based on said time of beat sequence, the IARS value indicative of a stress level of the regulatory adaptation systems of the patient; and
  a comparator configured to compare the IARS value to a first IARS threshold;
  wherein the electrical signal module configured to adjust the first electrical signal to provide a second electrical signal to the neural structure of the patient in response to the IARS value exceeding the first IARS threshold, the second electrical signal defined by a second set of signal parameter values, wherein at least one value of the second set of signal parameter values is different from a corresponding value in the first set of signal parameter values.

24. The medical device of claim 23, further comprising:
a memory unit configured to store the IARS value; and
a communications module configured to notify the patient, a healthcare provider, or both when the IARS value exceeds the first IARS threshold.

25. The medical device of claim 23, further comprising a lead interface, the lead interface being configured to provide the electrical signal to a lead configured to operatively couple, using an electrode, to at least one neural structure selected from among a portion of a brain structure of the patient, a cranial nerve of the patient, a spinal cord of the patient, a sympathetic nerve structure of the patient, and a vagus nerve of the patient.

26. The medical device of claim 23, wherein the chronic medical condition is at least one condition selected from among a traumatic brain injury; complications from stroke; a chronic cardiac disorder; obesity; a neuropsychiatric disorder selected from the group consisting of schizophrenia, depression, and borderline personality disorder; multiple sclerosis; fibromyalgia; and arthritis.

27. The medical device of claim 23, wherein the heart parameter module is configured to determine the first threshold IARS value based on the first baseline IARS value.

28. The medical device of claim 27, wherein the heart parameter module is configured to modify the first baseline IARS value to provide a second baseline IARS value based on a change in at least one of an environmental parameter and a patient-specific parameter, the heart parameter module further configured to adjust the first threshold IARS value to provide a new first threshold IARS value based on the second baseline IARS value.

29. The medical device of claim 23, wherein the at least one value of the second set of signal parameter values that is different from a corresponding value in the first set of signal parameter values is for at least one corresponding parameter selected from among a current amplitude, a pulse-width, a frequency, an on-time, and an off-time.

30. A medical device for adapting treatment of a patient having a chronic medical condition during periods of heightened stress on regulatory adaptation systems of the patient, comprising:
an electrical signal module configured to apply a first electrical signal to a cranial nerve of the patient to treat the chronic medical condition, the first electrical signal defined by a first set of signal parameter values;
a heart beat data processing module configured to determine a time of beat sequence of the patient's heart by sensing the time of beat sequence of the patient's heart and processing the data relating to the beat sequence to generate a time series data stream from said time of beat sequence;
a heart parameter module configured to determine a first index of activity of regulatory systems (JARS) value based on said time of beat sequence, the first IARS value indicative of a stress level of the regulatory adaptation systems of the patient; and
a comparator configured to compare the first IARS value to a first IARS threshold;
wherein the electrical signal module configured to adjust the first electrical signal to provide a second electrical signal to the cranial nerve of the patient in response to the first IARS value exceeding the first IARS threshold, the second electrical signal defined by a second set of signal parameter values, wherein at least one value of the second set of signal parameter values is different from a corresponding value in the first set of signal parameter values.

31. The medical device of claim 30, further comprising:
a memory unit configured to store the first IARS value; and
a communications module configured to notify the patient, a healthcare provider, or both when the first IARS value exceeds the first IARS threshold.

* * * * *